US006561992B1

(12) United States Patent
Eberhart et al.

(10) Patent No.: US 6,561,992 B1
(45) Date of Patent: May 13, 2003

(54) METHOD AND APPARATUS UTILIZING COMPUTATIONAL INTELLIGENCE TO DIAGNOSE NEUROLOGICAL DISORDERS

(75) Inventors: Russell C. Eberhart, Indianapolis, IN (US); Robert M. Worth, Indianapolis, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/655,635

(22) Filed: Sep. 5, 2000

(51) Int. Cl.$^7$ .......................... A61B 5/103; A61B 5/117
(52) U.S. Cl. ........................ 600/595; 600/300; 706/924
(58) Field of Search ................................ 600/300, 301, 600/595; 128/920, 922, 923, 924, 925; 706/6, 14, 15, 45–47, 61, 924

(56) References Cited

U.S. PATENT DOCUMENTS

| | | | | |
|---|---|---|---|---|
| 5,197,489 A | | 3/1993 | Conlan ........................ 600/595 |
| 5,265,619 A | | 11/1993 | Comby et al. ............... 600/595 |
| 5,293,879 A | | 3/1994 | Vonk et al. .................. 600/595 |
| 5,533,519 A | * | 7/1996 | Radke et al. ................ 600/595 |
| 5,762,072 A | * | 6/1998 | Conlan et al. ............... 600/595 |
| 6,306,087 B1 | * | 10/2001 | Barnhill et al. .............. 600/300 |

OTHER PUBLICATIONS

Smith, Dr. Leslie, "An Introduction to Neural Networks", published at least as early as Oct. 25, 1996 (8 pages).
IEEE Engineering in Medicine and Biology, "Early Detection of Parkinson's Disease Through Automatic Movement Evaluation", Mar./Apr. 1998 edition, pp. 81–88.
Orsnes et al., "Evaluation of Electronic Equipment for Quantitative Registration of Tremor", Sep. 16, 1997, pp. 36–40.
C.N. Riviere et al., "Adaptive Fourier Modeling for Quantification of Tremor", Journal of Neuroscience Methods 74, Oct. 22, 1996, pp. 77–87.

J. Timmer et al., "Quantitative Analysis of Tremor Time Series", Electroencephalography and Clinical Neurophysiology 101, Mar. 20, 1996, pp. 461–468.
Van Someren et al., "A New Actigraph for Long–Term Registration of the Duration and Intensity of Tremor and Movement", IEEE Transactions on Biomedical Engineering—vol. 45, No. 3, Mar. 1998, pp. 386–395.
Findley, Leslie J., "Classification of Tremors", Journal of Clinical Neurophysiology—vol. 13, No. 2, 1996, pp. 122–132.
"Particle Swarm Optimization Homepage", Mar. 4, 1999 (2 pages).
"What is Fuzzy Logic", Apr. 15, 1993 (3 pages).
Elble, Rodger J., MD, PhD, "Tremor in Ostensibly Normal Elderly People", Movement Disorders—vol. 13, No. 3, 1998, pp. 457–464.
Shi et al., "Implementations of Evolutionary Fuzzy Systems", IEEE Transactions on Fuzzy Systems—vol. 7, No. 2, Apr. 1999 (12 pages).

* cited by examiner

Primary Examiner—Kevin Shaver
Assistant Examiner—Charles Marmor, II
(74) Attorney, Agent, or Firm—Maginot, Moore & Bowman

(57) ABSTRACT

A method of diagnosing patients suspected of having a neurological disorder is disclosed and includes monitoring movement of a patient in order to obtain movement data that is representative of the movement of the patient. Another step of the method includes processing the movement data in order to obtain an input pattern that is representative of the movement data. The method also includes the step of processing the input pattern with a computational intelligence system that has been trained to classify movement based upon a predetermined group of neurological disorder classifications. Furthermore, the method includes generating with the computational intelligence system an output that is indicative of an appropriate neurological disorder classification for the patient. An analysis system for diagnosing patients suspected of having a neurological disorder is also disclosed.

30 Claims, 12 Drawing Sheets

METHOD AND APPARATUS UTILIZING COMPUTATIONAL INTELLIGENCE TO DIAGNOSE NEUROLOGICAL DISORDERS

FIELD OF THE INVENTION

The present invention relates generally to diagnosing neurological disorders, and more particularly to a method and apparatus which utilize a trained computational intelligence system to classify movement of a patient based upon neurological disorder classifications.

BACKGROUND OF THE INVENTION

Several symptoms associated with Parkinson's disease (PD) have been documented such as lack of facial expression, tremor of the distal segments of the limbs at rest, muscular rigidity, bradykenesia, and postural abnormalities. However, the exact diagnosis of PD in an early phase of the disease is complicated because other neurological disorders such as essential tremor (ET) have similar early symptoms. According to international statistics, the diagnosis of more than 20% of patients in an early phase of a neurological disorder is false. Moreover, the diagnosis for a great number of patients is typically uncertain in the first 2–3 years of the neurological disorder. This 2–3 years of uncertainty results in a more expensive and less effective treatment of the patient when compared with appropriate treatment started in an earlier phase of the disorder.

Therefore a need exists for a method and apparatus that are operable to accurately diagnose neurological disorders in an early phase of the disorder.

Definition of Terms Associated with Computational Intelligence

Computational intelligence as used herein refers to a methodology involving computing (usually with a computer) that exhibits an ability to learn and/or to deal with new situations, such that the system is perceived to possess one or more attributes of reason, such as generalization, discovery, association, and abstraction. Computational intelligence systems usually comprise hybrids of paradigms such as artificial neural networks, fuzzy systems, and evolutionary computation systems, augmented with knowledge elements. Computational intelligence systems are often designed to mimic one or more aspects of biological intelligence.

A paradigm as used herein refers to a particular choice of computational intelligence attributes—in the case of a neural network, the architecture, activation and learning rules, update procedure, and so on—that exhibits a certain type of behavior. In other words, a paradigm is a specific example of a computational intelligence system.

An artificial neural network (ANN) is used herein to refer to an analysis paradigm that is roughly modeled after the massively parallel structure of a biological neural network such as the human brain. An ANN is typically implemented with many relatively simple processing elements (PEs) that are interconnected by many weighted connections in order to obtain a computational structure that simulates the highly interconnected, parallel computational structure of biological neural networks. Hereinafter, the terms network and neural network are used interchangeably with the term artificial neural network.

The term evolutionary computation is used herein to refer to machine learning optimization and classification paradigms that are roughly based on evolutionary mechanisms such as biological genetics and natural selection. The evolutionary computational field includes genetic algorithms, evolutionary programming, genetic programming, evolution strategies, and particle swarm optimization.

Genetic algorithms are search algorithms that incorporate natural evolution mechanisms including crossover, mutation, and survival of the fittest. Genetic algorithm paradigms work on populations of individuals, rather than on single data points or vectors. Genetic algorithms are more often used for optimization, but may also be used for classification.

Evolutionary programming algorithms are similar to genetic algorithms, but do not incorporate crossover. Rather, evolutionary programming algorithms rely on survival of the fittest and mutation.

A particle swarm, as used herein, is similar to a genetic algorithm (GA) in that the system is initialized with a population of randomized positions in hyperspace that represent potential solutions to an optimization problem. However, each particle of a particle swarm, unlike a GA, is also assigned a randomized velocity. The particles (i.e. potential solutions) are then "flown" through hyperspace based upon their respective velocities in search of an optimum solution to a global objective.

Fuzzy sets model the properties of imprecision, approximation, or vagueness. In conventional logic an element either is or is not a member of the set. In other words, in conventional logic each element has a membership value of either 1 or 0 in the set. In a fuzzy set, however, each fuzzy membership value reflects the membership extents (or grades) of an element in the set which is often represented with values ranging between and including 0 and 1.

Fuzzy logic is the logic of "approximate reasoning." Fuzzy logic comprises operations on fuzzy sets including equality, containment, complementation, intersection, and union.

A fuzzy expert system as used herein, is a decision support rule-based expert system that uses fuzzy rules and fuzzy sets. A fuzzy expert system is more compact (i.e. has fewer roles) than traditional expert systems, and the rules are more consistent with the way knowledge is expressed in natural language. The system can represent multiple cooperating, and even conflicting experts.

The above terms as well as others associated with computational intelligence systems are defined in further detail in Russell C. Eberhart, et al., *Computational Intelligence PC Tools* (1996), the disclosure of which is hereby incorporated by reference.

SUMMARY OF THE INVENTION

The present invention is directed toward fulfilling the need for a method and apparatus that are operable to accurately diagnose neurological disorders. In accordance with one embodiment of the present invention, there is provided a method of diagnosing patients suspected of having a neurological disorder. One step of the method includes monitoring movement of a patient in order to obtain movement data that is representative of the movement of the patient. Another step of the method includes processing the movement data in order to obtain an input pattern that is representative of the movement data. The method also includes the step of processing the input pattern with a computational intelligence system that has been trained to classify movement based upon a predetermined group of neurological disorder classifications. Furthermore, the method includes generating with the computational intelligence system an output that is indicative of an appropriate neurological disorder classification for the patient.

Pursuant to another embodiment of the present invention, there is provided an analysis system for diagnosing patients suspected of having a neurological disorder. The analysis system includes a movement monitoring device, a preprocessor, and computational intelligence. The movement monitoring device of the analysis system is operable to monitor movement of a patient over a collection period in order to obtain movement data that is representative of the movement of the patient over the collection period. The preprocessor of the analysis system is operable to generate an input pattern that is representative of the movement data collected by the movement monitoring device over the collection period. The computational intelligence system includes a neural network that has been trained to classify movement based upon a predetermined group of neurological disorder classifications. In particular, the neural network is operable to (i) process the input pattern generated by the preprocessor, and (ii) generate an output that is indicative of an appropriate neurological disorder classification for the patient.

Pursuant to yet another embodiment of the present invention, there is provided a computer readable medium that configures an analysis system for diagnosing patients suspected of having a neurological disorder. The computer readable medium includes instructions which when executed by the analysis system cause the analysis system to generate an input pattern from movement data representative of movement of a patient over a collection period. The instructions of the computer readable medium when executed by the analysis system further cause the analysis system to implement a neural network trained to classify the movement of the patient based upon a predetermined group of neurological disorder classifications. Moreover, the instructions when executed by the analysis system cause the analysis system to process the input pattern with the neural network to obtain an appropriate neurological disorder classification for the patient. The instructions of the computer readable medium when executed by the analysis system also cause the analysis system to display output providing an indication of the appropriate neurological disorder classification for the patient.

It is an object of the present invention to provide a new and useful method and apparatus for diagnosing neurological disorders.

It is also an object of the present invention to provide an improved method and apparatus for diagnosing neurological disorders.

It is another object of the present invention to provide a method and apparatus for diagnosing a neurological disorder in an early phase of the neurological disorder.

It is yet another object of the present invention to provide a method and apparatus which utilize trained computational intelligence to classify movement based upon neurological disorder classifications.

The above and other objects, features, and advantages of the present invention will become apparent from the following description and the attached drawings.

DETAILED DESCRIPTION OF EXEMPLARY EMBODIMENTS

Figure 1:
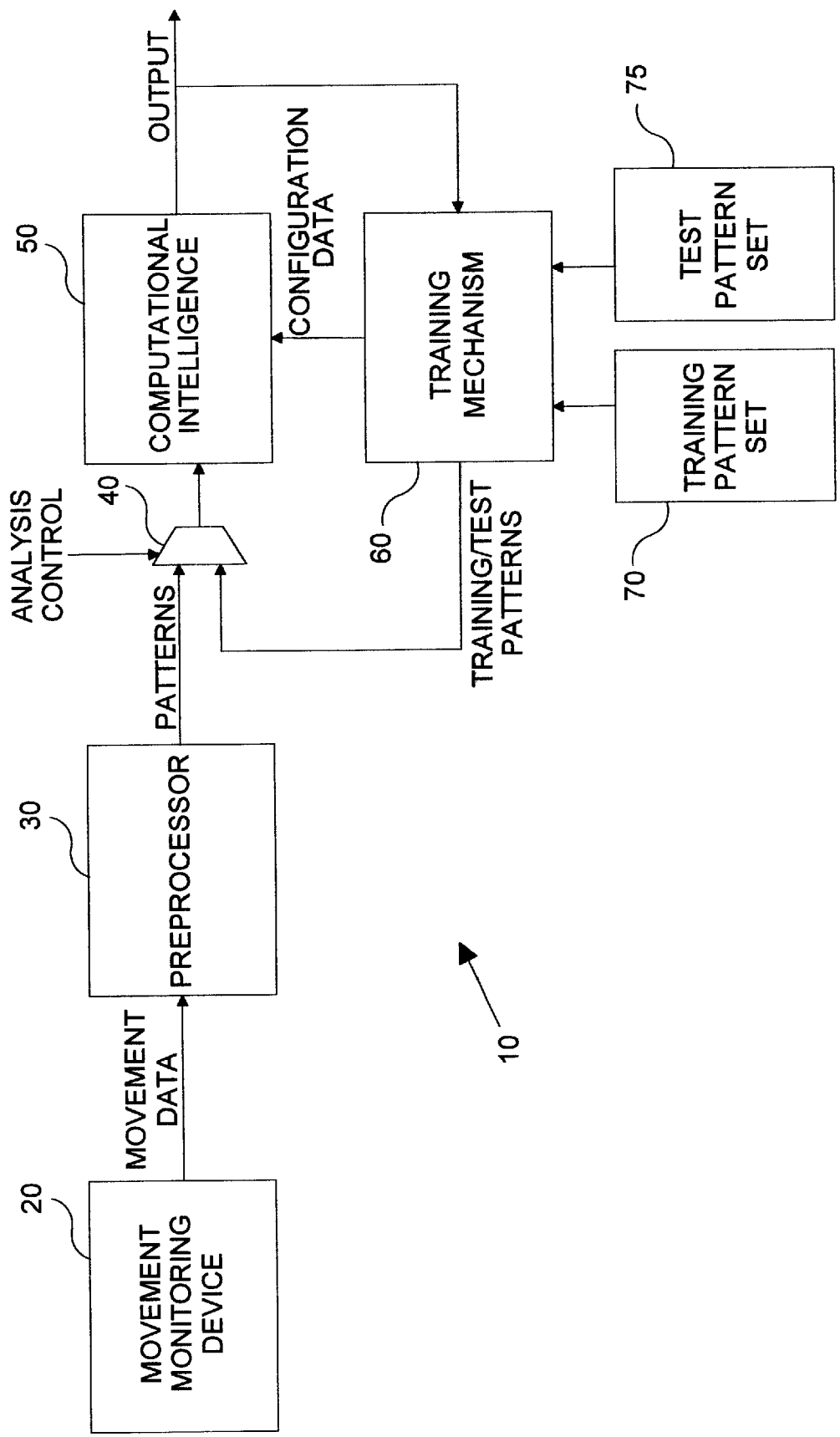
FIG. 1 shows a block diagram of an exemplary analysis system which incorporates features of the present invention therein.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIG. 1, an exemplary analysis system 10 is shown which incorporates various features of the present invention therein. In general, the exemplary analysis system 10 is operable to (i) monitor movement of a patient, and (ii) classify the monitored movement as being characteristic of a certain neurological disorder. More specifically, the exemplary analysis system 10 is operable to (i) collect movement data that is representative of movement of a patient over a collection period, (ii) process the collected movement data, and (iii) generate output that indicates whether the movement of the patient during the collection period is indicative of a person who has Parkinson's disease (PD) or essential tremor (ET). To this end, the exemplary analysis system 10 includes a movement monitoring device 20, a preprocessor 30, a multiplexor 40, and a computational intelligence system 50.

The movement monitoring device 20 is generally operable to monitor movement of a patient, and produce movement data that generally represents the movement of the patient. More specifically, the movement monitoring device 20 in an exemplary embodiment is operable to produce an analog movement signal having an amplitude that varies with respect to time based upon movement of the patient being monitored. In particular, in an exemplary embodiment, the movement monitoring device 20 is operable to vary the amplitude of the analog movement signal such that the analog movement signal has a resolution of about 10 milliG's (i.e. ten one thousandths of Earth's gravitational force) and a temporal resolution of at least 25 samples per second.

The preprocessor 30 is operable to receive movement data from the movement monitoring device 20, and process the movement data to obtain preprocessed movement data having a form suitable for processing by the computational intelligence system 50. More specifically, the preprocessor 30 in an exemplary embodiment is operable to receive the movement data from the movement monitoring device 20, extract characteristics of the movement from the movement data, generate data patterns from the extracted characteristics of the movement data, and provide the computational intelligence system 50 with the generated data patterns via the multiplexor 40.

The multiplexor 40 is operable to receive data patterns from the preprocessor 30 and a training mechanism 60, and provide the computational intelligence system 50 with the data patterns originating from either the preprocessor 30 or the training mechanism 60 based upon the state of an analysis control signal.

In general, the computational intelligence system 50 is operable to receive preprocessed movement data from the preprocessor 30, and analyze the preprocessed movement data. More specifically, the computational intelligence system 50 in an exemplary embodiment is trained to classify movement based upon a data pattern received from the preprocessor 30 and a predetermined group of neurological disorder classifications. In particular, the computational intelligence system 50 of an exemplary embodiment is operable to generate an output that is indicative of an appropriate neurological disorder classification based upon the received data pattern and a predetermined group of neurological disorder classifications that include a normal classification, a Parkinson's disease classification, and an essential tremor classification. In yet another exemplary embodiment, the computational intelligence system 50 is operable to generate an output that is indicative of an appropriate neurological disorder classification based upon the received data pattern and a predetermined group of neurological disorder classifications that include a normal tremor classification, and a non-normal tremor classification (e.g. a classification encompassing both PD and ET).

Implementation of the Movement Monitoring Device

As stated above, the movement monitoring device 20 essentially monitors the movement of a patient and generates movement data that is representative of the monitored movement. To this end, the movement monitoring device 20 in an exemplary embodiment is implemented with a TeleActigraph (TAG) produced by Precision Control Design, Inc. (PCD) of Fort Walton Beach, Fla. In particular, the PCD TAG includes a wrist-mounted actigraph 80 that samples an analog movement signal at a rate of about 27 Hz with about a 12-bit resolution, and transmits the resulting 12-bit digital samples via a 300 MHz wireless link to a belt-worn unit that is operable to store up to about 5 Megabytes of data or roughly 5 hours and 20 minutes of data. Alternatively, a wrist-mounted actigraph similar to Precision Control Design's model number BMA-32 but lacking a belt-worn unit is described in detail in U.S. Pat. No. 5,197,489, the disclosure of which is hereby incorporated by reference.

Figure 2:
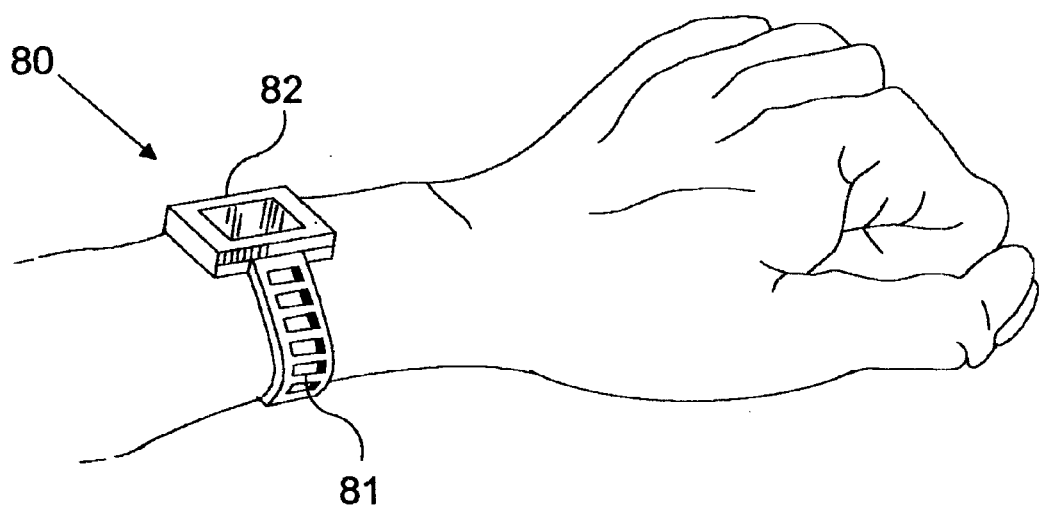
FIG. 2 shows a wrist-mounted actigraph suitable for implementing the movement monitoring device of FIG. 1.
Figure 3:
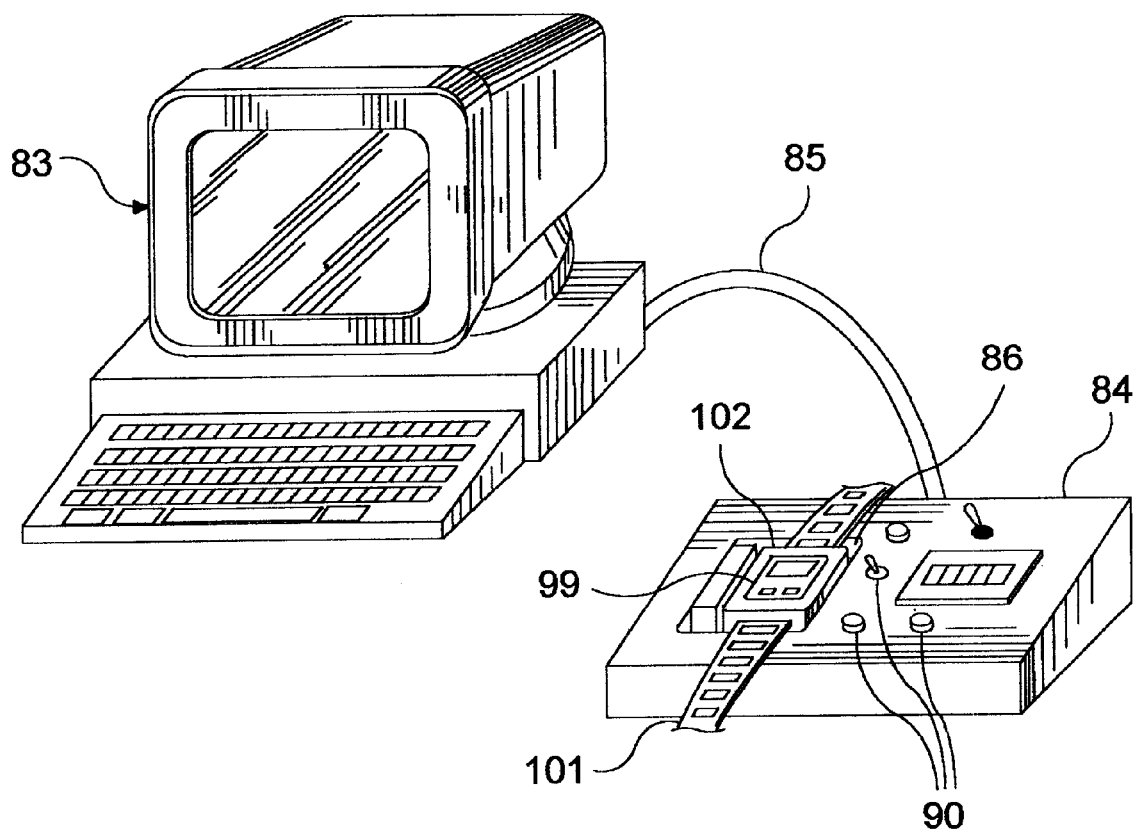
FIG. 3 shows a computer, interface unit, and a belt-worn unit used in conjunction with the wrist-mounted actigraph of FIG. 2.

As depicted in FIG. 2 and FIG. 3, the exemplary PCD TAG system includes a wrist-mounted actigraph 80 and a belt-worn unit 99. The wrist-mounted actigraph 80 is constructed to have a shape and size similar to a wrist-watch, and the belt-worn unit 99 is constructed to have a shape and size similar to a belt with a large belt buckle. More specifically, the belt-worn unit 99 includes a flexible band 101 which secures a generally rectangular housing 102 to the waist of a person. Similarly, the actigraph 80 includes a flexible band 81 which secures a generally rectangular housing 82 against the skin surface of a patient being monitored. Typically, the actigraph 80 is mounted on the non-dominant wrist of the patient which has been found to correlate well with body activity.

In use, the actigraph 80 and the belt-worn unit 99 are worn by the patient for a predetermined collection period such as a few minutes or several hours. During the collection period, a sensor circuit of the actigraph 80 generates an analog movement signal having a voltage amplitude that is modulated based upon activity of a person wearing the wrist-mounted actigraph 80. Moreover, an A/D converter of the actigraph 80 samples the analog movement signal at a sampling rate such as 27 Hz in order to obtain 12-bit digital samples of the analog movement signal generated by the sensor circuit. Furthermore, the actigraph 80 includes a transmitter which is operable to transfer the generate 12-bit digital samples to the belt-worn unit 99.

Data collected by the belt-worn unit 99 during the collection period is later downloaded to a computer 83 for further processing and analysis. More specifically, communication between the belt-worn unit 99 and the computer 83 is facilitated by an interface unit 84, which is connected to a data port of the computer 83 via a conventional RS-232 cable 85 or the like. The interface unit 84 preferably includes a receptacle 86 on its top surface dimensioned to receive the rectangular housing 102 of the belt-worn unit 99. An electrical connector located along one side of receptacle 86 engages a connector on housing 102 when the belt-worn unit 99 is seated within the receptacle 86. With this arrangement the belt-worn unit 99 can be quickly and conveniently installed and removed from interface unit 84.

The interface unit 84 enables data to be exchanged between the personal computer 83 and the PCD TAG system in both directions. The bi-directional nature of the data exchange enables (i) collected data to be downloaded from the PCD TAG system to the computer 83, and (ii) operating instructions to be uploaded from the computer 83 to the PCD TAG system which control the operation of the actigraph 80 in subsequent data collection assignments. A plurality of controls 90 on the top surface of interface unit 84 assist the operator in accomplishing the downloading and uploading functions.

General Operation of an Exemplary Analysis System

Figure 4:
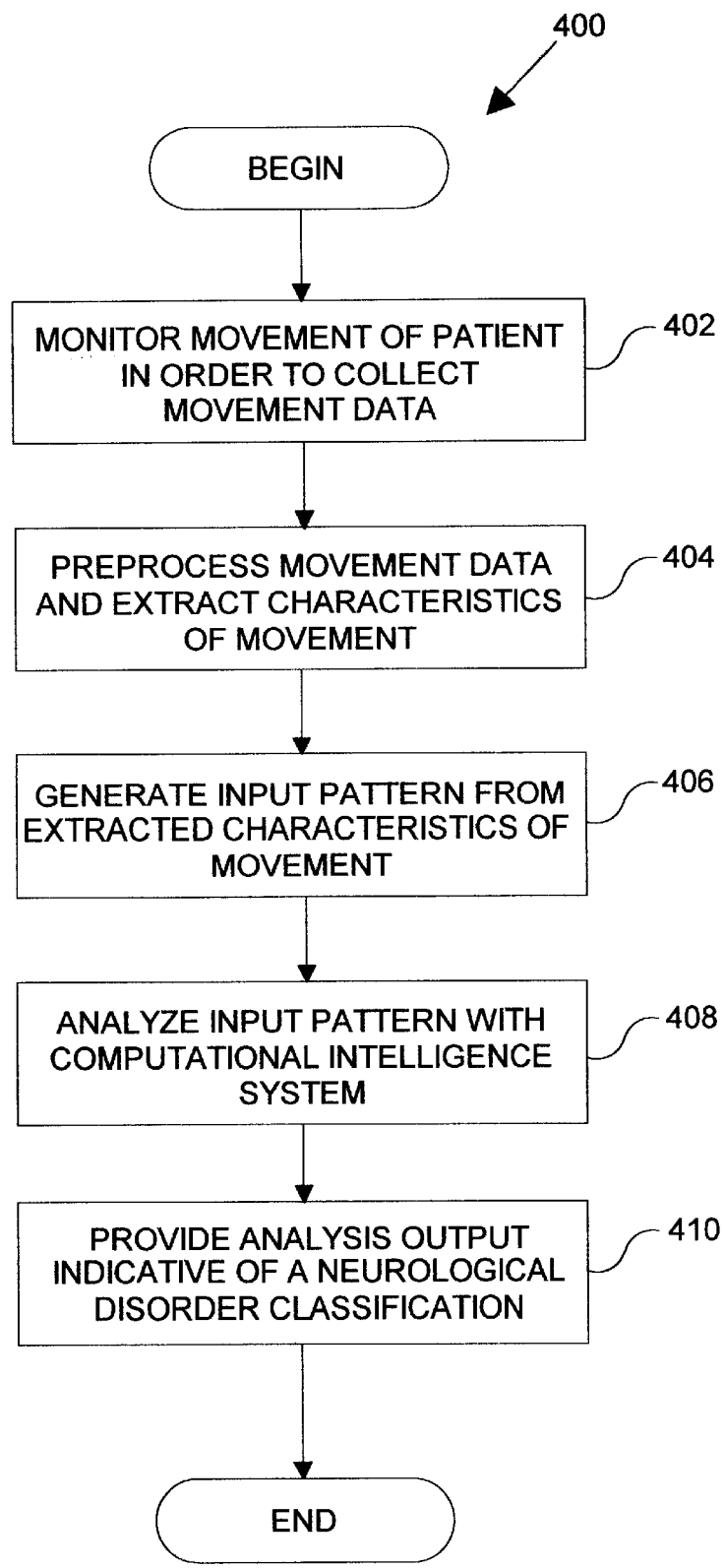
FIG. 4 shows a flowchart which illustrates the general operation of the analysis system of FIG. 1.

Shown in FIG. 4, there is illustrated a flowchart 400 that depicts the general operation of the exemplary analysis system 10. More specifically, the general operation of the analysis system 10 will be described in a manner which assumes the computational intelligence system 50 of the analysis system 10 has been properly trained to classify movement data based upon a group of predetermined neurological classifications that includes a normal classification, a PD classification, and an ET classification. In general, the normal classification corresponds to persons who exhibit movement indicative of normal physiologic tremor, the PD classification corresponds to persons who exhibit movement indicative of Parkinson's disease, and the ET classification corresponds to persons who exhibit movement indicative of essential tremor. Training of an exemplary embodiment of the computational intelligence system 50 to classify movement data based upon a group of predetermined neurological classifications is described in detail with reference to FIGS. 6, 7, 8A, 8B, 9, and 10.

As depicted in FIG. 4, the analysis system 10 begins in step 402 with the movement monitoring device 20 monitoring movement of a patient suspected of having a neurological disorder, and collecting movement data from the patient that is representative of the movement of the patient over a collection period. In an exemplary embodiment, collection of the movement data is accomplished by providing the PCD TAG system with operating instructions via the interface unit 84 and the computer 83, and then mounting the actigraph 80 of the PCD TAG system to the non-dominant wrist of the patient. More specifically, in an exemplary embodiment using the PCD TAG system, the system is set to mode 9 which results in configuring the actigraph 80 for low gain and a bandwidth of about 0.1 to about 14 Hz. In mode 9, the actigraph 80 has been found to generate digital samples between the ranges of about 1230 (−400) to about 2230 (+600) with a zero level of about 1630.

After mounting the actigraph 80 to the non-dominant wrist of the patient, the patient in an exemplary embodiment is asked to perform a series of postural movements with the non-dominant wrist so that the PCD TAG system may obtain movement data for different postural tremor types (e.g. postural tremor, rest tremor, and kinetic tremor). In particular, the patient in an exemplary embodiment of the analysis system 10 is requested to sit in a chair in front of a table and hold their non-dominant arm in a stationary horizontal position for a period of 1 minute in order to obtain postural tremor data from the patient. Afterwards, the patient is requested to rest their non-dominant hand on their thigh for a period of 1 minute in order to obtain rest tremor data. After obtaining the rest tremor data, the patient is requested to alternately touch his or her nose and the finger of a person sitting directly in front of them for a period of 1 minute in order to obtain kinetic tremor data.

During the above intervals of time, the actigraph 80 generates an analog movement signal that is representative of the movement of the patient over the collection period, digitizes the analog movement signal by sampling the analog movement signal at a predetermined sampling rate (e.g. 27 Hz), and stores the digital samples in a memory of the belt-worn unit 99. Accordingly, after the collection period is completed, the belt-worn unit 99 may be placed in the interface unit 84 so that the computer 83 may download the 12-bit digital samples that are representative of the movement of the patient during the collection period.

In step 404, the preprocessor 30 processes the movement data collected by the movement monitoring device 20 in order to extract characteristics of the movement which the computational intelligence system 50 is trained to analyze. To this end, the preprocessor 30 essentially discards obtained movement data that is likely not representative of movement of the patient, and extracts characteristics of the movement data from the retained movement data. More specifically, the actigraph 80 used to implement the exemplary movement monitoring device 20 requires some time to settle (warm up) once data collection is started. As a result, the first few digital samples produced by the actigraph 80 do not accurately represent activity of the patient. Moreover, the last few digital samples produced by the actigraph 80 also may not accurately represent activity of the patient due to the action required to stop the actigraph 80 from collecting movement data. Furthermore, samples associated with a transition between collecting different postural tremor data are also discarded to better ensure the associated samples are reflective of the desired postural tremor type.

For example, the preprocessor 30 in an exemplary embodiment discards the first 5 seconds and last 5 seconds worth of samples for each postural tremor type. In other words, assuming that 1 minutes worth of movement data is collected for each postural tremor type, the preprocessor after discarding the first 5 seconds and last 5 seconds of digital sample obtains 50 seconds worth of digital samples for each postural tremor type. In an exemplary embodiment, the actigraph 80 generates digital samples at a rate of approximately 27 Hz. Accordingly, the preprocessor 30 in the exemplary embodiment essentially retains about 1350 digital samples for each postural tremor type.

The exemplary preprocessor 30 then extracts characteristics of the movement of the patient from the movement data. For example, depending upon the type of information the computational intelligence system 50 was trained to analyze, the preprocessor 30 may extract frequency characteristics of the movement from the movement data by obtaining the power spectral density, the fast Fourier transform, or other frequency transform of the movement data. Moreover, the preprocessor 30 may extract statistical data such as the number of zero crossings during a time window or epoch, the maximum during an epoch, the minimum during an epoch, the average during an epoch, and the average power during an epoch.

In particular, the preprocessor 30 in an exemplary embodiment calculates power spectral density data from the remaining digital samples for each postural tremor type. More specifically, the exemplary preprocessor 30 for each tremor type performs a one hundred twenty-eight (128) point frequency transformation upon a sliding window of greater than two hundred and fifty-six (256) digital samples thus resulting in sixty-four (64) power spectral density data points for each window or epoch. For example, in an exemplary embodiment, the preprocessor 30 calculates sixty-four (64) power spectral density data points for each fifty seconds of digital samples.

Of the sixty-four (64) power spectral density data points, the exemplary preprocessor 30 discards the first two (2) data points and the last two (2) data points thus resulting in sixty (60) data points for each epoch which span a frequency range between roughly 0.5 Hz and 13 Hz. Assuming three (3) postural tremor types, and sixty (60) power spectral density points per postural tremor type, the exemplary preprocessor 30 obtains a total of 180 power spectral density points per patient. After obtaining power spectral density points that are representative of the movement of a single patient during the collection period, the preprocessor 30 takes the square root of each of the power spectral density points in order to obtain amplitude data points that are proportional to the amplitude of the movement. Furthermore, the preprocessor 30 further divides each of the amplitude data points by the largest amplitude data point in order to normalize the amplitude data points to a range between 0 and 1.

After extracting characteristics of the movement of the patient from the movement data, the preprocessor 30 in step 406 generates an input pattern $A_k$ for the computational intelligence system 50 from the extracted characteristics of the movement. In particular, the preprocessor 30 in an exemplary embodiment generates an input pattern $A_k$ having 180 input signals $a_{k1}, a_{k2}, \ldots a_{k180}$ where each input signal $a_{kx}$ is representative of one of the 180 extracted amplitude data points. It should be appreciated by those skilled in the art, that the preprocessor 30 may further include other extracted characteristics of the movement in the input pattern $A_k$ such as the number of zero crossings per epoch, and the average power of the movement per epoch if the computational intelligence system 50 is trained to process the additional characteristics.

In step 408, the computational intelligence system 50 analyzes the preprocessed movement data collected from the patient. To this end, the multiplexor 40 receives the input pattern $A_k$ from the preprocessor 30 and applies the input pattern $A_k$ to inputs of the computational intelligence system 50. More specifically, in an exemplary embodiment utilizing a trained neural network 100 for the computation intelligence 60, the inputs signal $a_{1k}$, $a_{2k}$, $a_{180k}$ of the input pattern $A_k$ are applied to the input layer $F_x$ of the trained neural network 100. As a result of the input pattern $A_k$ being applied to the input layer $F_x$, the trained neural network 100 generates an output pattern $Z_k$ that is indicative of an appropriate classification for the movement.

For example, in an exemplary embodiment, the trained neural network 100 of the computational intelligence system 50 is configured to generate an output pattern $Z_k$ having three output signals $Z_{1k}$, $Z_{2k}$, and $Z_{3k}$ each having a value between 0 and 1. The closer the first output signal $Z_{1k}$ is to 1 the more likely the person has Parkinson's disease and the closer the output signal $Z_{1k}$ is to 0 the more likely the person does not have Parkinson's disease. The closer the second output signal $Z_{2k}$ is to 1 the more likely the person has essential tremor and the closer the second output signal $Z_{2k}$ is to 0 the more likely the person does not have essential tremor. Furthermore, the closer the third output signal $Z_{3k}$ is to 1 the more likely the person exhibits normal physiologic tremor characteristics and the closer the third output signal $Z_{3k}$ is to 0 the more likely the person does exhibit normal tremor characteristics.

Finally in step 410, the analysis system 10 provides analysis output results such as an appropriate neurological disorder classification for the movement. More specifically, the analysis system 10 in an exemplary embodiment displays upon a monitor of the computer 83 a graphical plot of the 60 amplitude points for each postural tremor type (180 total), and the output pattern $Z_k$ generated by the computational intelligence system 50. Moreover, the analysis system 10 in an exemplary embodiment includes fuzzy logic that receives the output pattern $Z_k$ and generates an indication of whether the movement is indicative of (i) people who have Parkinson's disease, (ii) people who have essential tremor, (iii) people who exhibit normal tremor characteristics, or (iv) people with whom the analysis system 10 is unable to reach a conclusive result.

Alternatively, the neurological disorder classification information determined in step 410 may include one or more levels of severity for one or more previously identified neurological disorders. In such a system, neurological disorder classification information relating to disorder severity can be used in the quantitative evaluation of the efficacy of a treatment.

Implementation of Computational Intelligence System

While computational intelligence system 50 will be described in detail with reference to a neural network implementation that is trained and simplified with particle swarm optimization, it should be appreciated by those skilled in the art that the computational intelligence system 50 may be implemented with other computational intelligence paradigms. For example, the computational intelligence system 50 may be implemented with or include other neural network paradigms such as error back-propagation, and learning vector quantization (LVQ). Moreover, the computational intelligence system 50 may be implemented with or include other computational intelligence paradigms such as genetic algorithms, evolutionary algorithms, and fuzzy logic. The computational intelligence system 50 may also be implemented with or include hybrids of the basic computational intelligence paradigms. For example, the computational intelligence system 50 may include a fuzzy expert system whose rules and membership functions are automatically evolved from training data patterns via an LVQ neural network, genetic algorithms, and particle swarm optimization. A method of evolving a fuzzy expert system from training patterns sets is described in detail in Yuhui Shi, et al., Implementation of Evolutionary Fuzzy Systems, *IEEE Transactions on Fuzzy Systems,* Vol. 7, No. 2, April 1999 at 109, the disclosure of which is hereby incorporated by reference.

Figure 5:
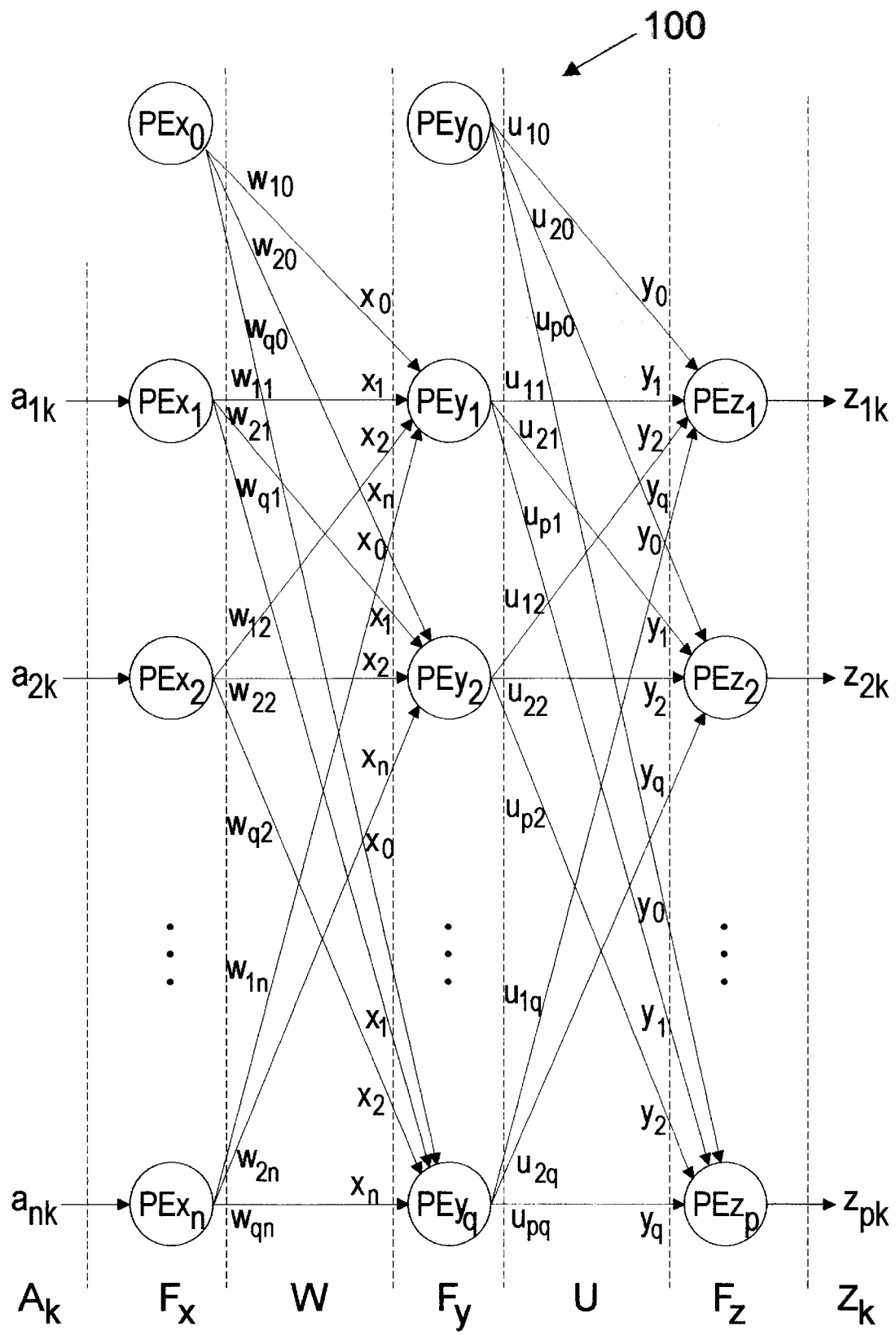
FIG. 5 shows an exemplary neural network suitable for implementing the computational intelligence system of FIG. 1.

Referring now to FIG. 5, there is illustrated an exemplary neural network 100 for implementing the computational intelligence system 50 of the exemplary analysis system 10. As depicted, the neural network 100 includes an input layer $F_x$ of processing elements $PEx_0$, $PEx_1$, ... $PEx_n$, a hidden layer $F_Y$ of processing elements $PEy_0$, $PEy_1$, ... $PEy_q$, and an output layer $F_Z$ of processing elements $PEz_1$, $PEz_2$, ... $PEz_p$. In general, each processing element $PEx_h$ of the input layer $F_X$ is coupled to each processing element $PEy_i$ of the hidden layer $F_Y$ via a matrix of weighted connections W. Moreover, each processing element $PEy_i$ of the hidden layer $F_y$ is coupled to each processing element $PEz_j$ of the output layer $F_Z$ via a matrix of weighted connections U.

The exemplary neural network 100 of FIG. 5 is commonly referred to as a fully connected feed-forward neural network since a weighted connection exists between each processing element of adjacent layers and no signal path of the neural network 100 passes through a processing element more than once. While the exemplary neural network 100 is a fully connected feed-forward neural network, it should be appreciated by those skilled in the art that the neural network 100 could alternatively be implemented with sparsely connected neural network topologies, randomly connected neural network topologies, and/or feed-back neural network topologies.

Referring to FIG. 5 in more detail, the input layer $F_X$ of the neural network 100 includes a biasing processing element $PEx_0$ and input processing elements $PEx_1$, $PEx_2$, ... $PEx_n$. The biasing processing element $PEx_0$ essentially provides an internal bias for each of the hidden processing elements $PEy_1$, $PEy_2$, ... $PEy_q$. To this end, the biasing processing element $PEx_0$ of the input layer $F_x$ is operable to generate a constant output signal $x_0$ (e.g. a signal having a value of 1) which is propagated to the hidden processing elements $PEy_1$, $PEy_2$, ... $PEy_q$ via weighted connections $w_{10}$, $w_{20}$, ... $w_{q0}$ of the weighted connections matrix W.

The input processing elements $PEx_1$, $PEx_2$, ... $PEx_n$ essentially distribute input signals $a_{1k}$, $a_{2k}$, ... $a_{nk}$ of an input pattern $A_k$ to the hidden processing elements $PEy_1$, $PEy_2$, ... $PEy_q$. To this end, each input processing element $PEx_h$ is operable to (i) receive a single input signal $a_{hk}$ of the input pattern $A_k$, and (ii) generate a corresponding output signal $x_h$ which is propagated to the hidden processing elements $PEy_1$, $PEy_2$, ... $PEy_q$ via the weighted connections matrix W. More specifically, each input processing element $PEx_h$ of the exemplary neural network 100 is operable to generate an output signal $x_h$ that is equal to its respective input signal $a_{hk}$. Moreover, the weighted connections $w_{1h}$, $w_{2h}$, ... $w_{qh}$ associated with each input processing element $PEx_h$ are operable to propagate the generated output signal $x_h$ to each of the hidden layer processing elements $PEy_1$, $PEy_2$, ... $PEy_q$.

The hidden layer $F_y$ of the neural network 100 includes a biasing processing element $PEy_0$ and the hidden processing elements $PEy_1$, $PEy_2$, ... $PEy_q$. The biasing processing element $PEy_0$ essentially provides an internal bias for each of the output processing elements $PEz_1, PEz_2, \ldots PEz_p$. To this end, the biasing processing element $PEy_0$ of the hidden layer $F_y$ is operable to generate a constant output signal $y_0$ (e.g. a signal having a value of 1) which is propagated to the output processing elements $PEz_1, PEz_2, \ldots PEz_p$ via weighted connections $u_{10}, u_{20}, \ldots u_{p0}$ of the weighted connections matrix U.

The hidden processing elements $PEy_1, PEy_2, \ldots PEy_q$ essentially generate output signals $y_1, y_2, \ldots y_q$ that are a function of the received output signals $x_0, x_1, \ldots x_n$ and weighted connections W. More specifically, each hidden processing element $PEy_I$ generates an output signal $y_i$ that is a function of the received output vector X (i.e. output signals $x_0, x_1, \ldots x_n$) and associated weighted connections vector $W_i$ (i.e weighted connections $w_{i0}, w_{i1}, \ldots w_{in}$. Accordingly, each output signal $y_i$ of the hidden processing elements $PEy_1, PEy_2, \ldots PEy_q$ may be represented mathematically as follows:

$$y_i = F(X, W_i) \quad (1)$$

where F represents the processing element function which is also commonly referred to as the activation function of the processing element.

In implementing the activation function F, each hidden processing element $PEy_i$ of the exemplary neural network 100 performs a combinatory function c( ) of its corresponding inputs X and $W_i$ and passes the resulting combinatory value c through a threshold function f( ). More specifically, each hidden processing element $PEy_i$ of the exemplary neural network 100 performs a linear combination (i.e. dot product) of its corresponding inputs X and $W_i$ and passes the resulting dot product value c through a sigmoid threshold function. The following hidden layer signal equation (2) represents the output signal $y_i$ as a threshold function f( ) of the combinatory function c( ) where the combinatory function c( ) is implemented as the linear combination of inputs X and $W_j$:

$$y_i = f(c(X, W_i)) = f(X \cdot W_i) = f\left(\sum_{m=0}^{n} x_m w_{im}\right) \quad (2)$$

The following equation (3) represents the sigmoid threshold function used by each hidden processing element $PEy_i$.

$$f(x) = \frac{1}{1 + e^{-\alpha x}} \quad (3)$$

where $\alpha$ represents a slope factor of the sigmoid function that in essence scales the inputs X and $W_i$ of the hidden processing element $PEy_i$.

The output layer $F_z$ of the neural network 100 includes the output processing elements $PEz_1, PEz_2, \ldots PEz_p$. The output processing elements $PEz_1, PEz_2, \ldots PEz_p$ essentially generate output signals $z_{1k}, z_{2k}, \ldots z_{pk}$ that are a function of the received hidden layer output signals $y_0, y_1, \ldots y_q$ and the weighted connections matrix U. More specifically, each output processing element $PEz_j$ generates an output signal $z_j$ that is a function of a received output vector Y (i.e. output signals $y_0, Y_1, \ldots y_q$) and associated weighted connection vector $U_j$ (i.e. weighted connections $u_{j0}, u_{j1}, u_{jp}$). Accordingly, each output signal $z_j$ of the output processing elements $PEz_1, PEz_2, \ldots PEz_p$ may be represented mathematically as follows:

$$z_j = F(Y, U_j) \quad (4)$$

where F represents the activation function of the processing element function.

In implementing the activation function F, each output processing element $PEz_j$ of the exemplary neural network 100 performs a combinatory function c( ) of its corresponding inputs Y and $U_j$ and passes the resulting combinatory value c through a threshold function f( ). More specifically, each output processing element $PEz_j$ of the exemplary neural network 100 performs a linear combination (i.e. dot product) of its corresponding inputs Y and $U_j$ and passes the resulting dot product value c through a sigmoid threshold function. The following output layer signal equation (5) represents the output signal $z_j$ as a threshold function f( ) of the combinatory function c( ) where the combinatory function c( ) is implemented as the linear combination of inputs Y and $U_j$:

$$z_j = f(c(Y, U_j)) = f(Y \cdot U_j) = f\left(\sum_{m=0}^{q} y_m u_{jm}\right) \quad (5)$$

where f( ) represents the above sigmoid threshold function which is presented again with a slope factor of $\beta$ instead of $\alpha$ so that the slope factors $\beta_1, \beta_2, \ldots \beta_p$ of the output processing elements $PEz_1, PEz_2, \ldots PEz_p$ are easily distinguishable from the slope factors $\alpha_1, \alpha_2, \ldots \alpha_q$ of the hidden processing elements $PEy_1, PEy_2, \ldots PEy_q$:

$$f(x) = \frac{1}{1 + e^{-\beta x}} \quad (6)$$

During operation, the neural network 100 essentially receives an input pattern $A_k$ and generates a respective output pattern $Z_k$ based upon the processing element activation functions F and weighted connections matrices W and U. More specifically, the input layer $F_x$ receives an input pattern $A_k$ of input signals $a_{1k}, a_{2k}, \ldots a_{nk}$, and generates a corresponding input layer signals $x_1, x_2, \ldots x_n$ that are propagated to the hidden layer $F_y$ via the weighted connections matrix W. Moreover, the input layer $F_x$ generates a biasing signal $x_0$ that is also propagated to the hidden layer $F_y$ via the weighted connections matrix W. The hidden layer $F_y$ then generates hidden layer signals $y_1, y_2, \ldots y_q$ that are based upon the received biasing signal $x_0$, the input layer signals $x_1, x_2, \ldots x_n$, the weighted connections matrix W, and the activation functions F of the hidden processing elements $PEy_1, PEy_2, \ldots PEy_q$. Moreover, hidden layer $F_y$ generates a biasing signal $y_0$ which is propagated along with the hidden layer signals $y_1, y_2, \ldots y_q$ to the output layer $F_z$ via the weighted connections matrix U. The output layer $F_z$ then generates output signals $z_{1k}, z_{2k}, \ldots z_{pk}$ based upon the received biasing signal $y_0$, the hidden layer signals $y_1, y_2, \ldots y_n$, weighted connections matrix U, and the activation functions F of the output processing elements $PEz_1, PEz_2, \ldots PEz_p$.

While the input processing elements $PEx_1, PEx_2, \ldots PEx_n$ of the exemplary neural network 100 essentially implement an identity activation function F( ) that generates an output signal that is equal to a received input signal, the input processing elements $PEx_1, PEx_2, \ldots PEx_n$ may also be implemented in a manner similar to the processing elements of the hidden layer $F_y$ and the output layer $F_z$. Moreover, while the processing elements of the hidden layer $F_y$ and the output layer $F_z$ utilize a linear combination function and a sigmoid threshold function, it should be appreciated by those skilled in the art that the activation functions F( ) of the processing elements may be implemented in several other known manners. More specifically, the activation function F( ) may use a different combinatory function c( ) and pass the combinatory result c through a different threshold function f( ). For example, TABLE 1 discussed below lists several alternatives for the threshold function f( ). Moreover, it should be appreciated that while the exemplary processing elements combine the received signals and pass the result through a threshold function, the activation function F( ) may be implemented in such a manner as to generate an output signal directly from the received signals without first performing a combinatory function of the received inputs.

General Operation for Obtaining Training and Testing Data Sets

Figure 6:
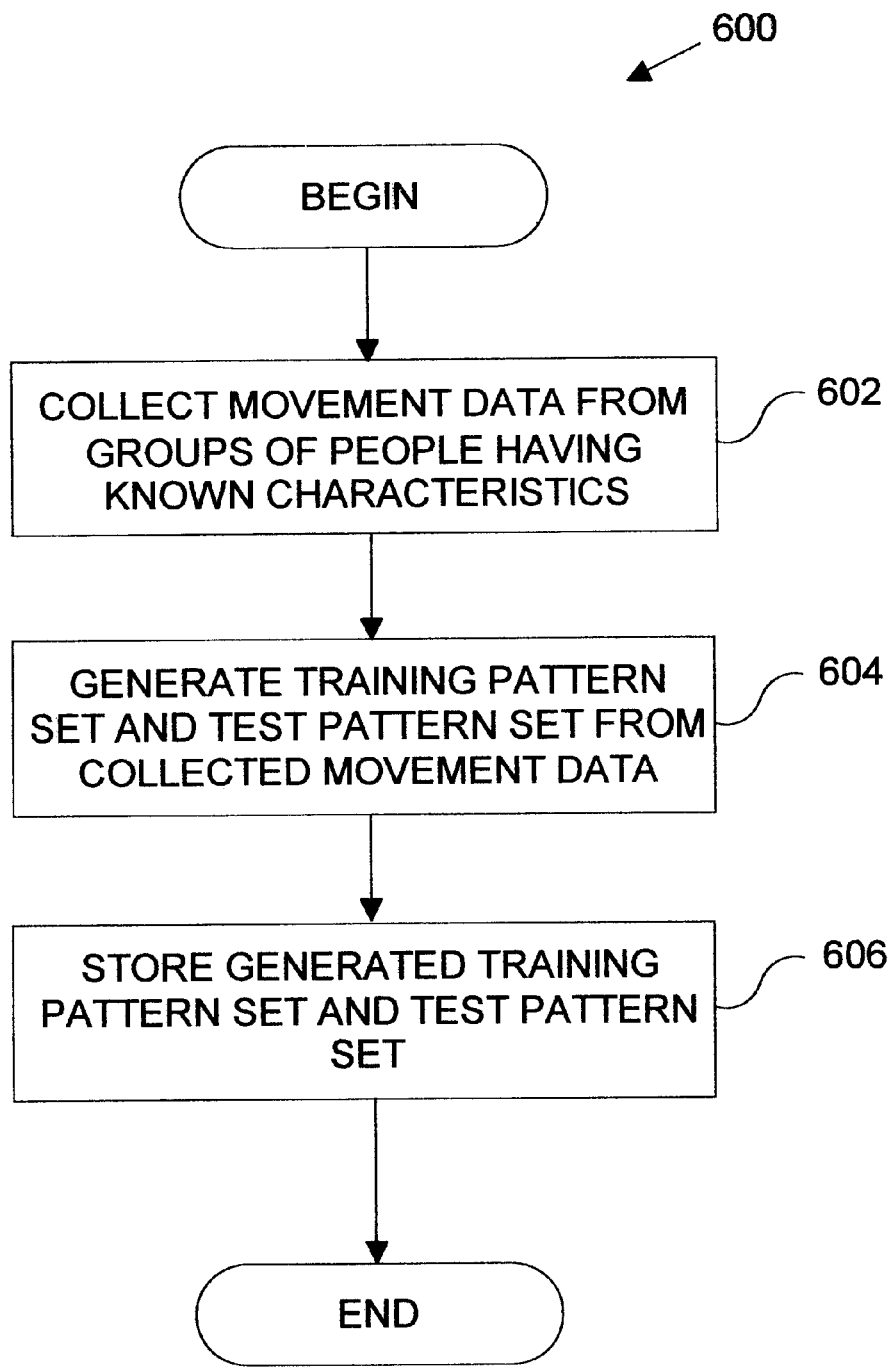
FIG. 6 shows a flowchart of an exemplary method of obtaining a training pattern set and a test pattern set suitable for training and testing the computational intelligence system of FIG. 1.

Shown in FIG. 6, there is illustrated a flowchart 600 that depicts the general operation of obtaining a training pattern set $TRAIN_{SET}$ and a test pattern set $TEST_{SET}$ for training and testing the computational intelligence system 50 of the analysis system 10. More specifically, the general operation of obtaining a training pattern set $TRAIN_{SET}$ and a test pattern set $TEST_{SET}$ will be described in a manner which assumes the computational intelligence system 50 of the analysis system 10 will be trained to distinguish movement associated with a normal classification, a PD classification, and a ET classification. Training a neural network 100 of the computational intelligence system 50 with the training pattern set $TRAIN_{SET}$ to distinguish between movement associated with a normal classification, a PD classification, and an ET classification is described in detail below with reference to FIGS. 7, 8A, 8B, 9, and 10.

As depicted in FIG. 6, the analysis system 10 begins in step 602 with the movement monitoring device 20 collecting movement data from a group of people who are known to have Parkinson's disease, a group of people who are known to have essential tremor, and a group of people who are known to exhibit normal physiologic tremor characteristics. In an exemplary embodiment, collection of the movement data is accomplished by providing the PCD TAG system with operating instructions via the interface unit 84 and the computer 83, and then mounting the actigraph 80 to the non-dominant wrist of each person for a separate collection period. More specifically, in an exemplary embodiment, the PCD TAG system is set to mode 9 which results in configuring the actigraph 80 for low gain and a bandwidth of about 0.1 to about 14 Hz.

After mounting the actigraph 80 to the non-dominant wrist of a person from one of the target groups, the person is requested to perform a series of postural movements with the non-dominant wrist so that the actigraph 80 may obtain movement data representative of different postural tremor types. In particular, the person in an exemplary embodiment of the analysis system 10 is requested to sit in a chair in front of a table and hold their non-dominant hand elevated in a stationary horizontal position for a period of 1 minute in order to obtain postural tremor data from the person. Afterwards, the person is requested to rest their non-dominant hand on their thigh for a period of 1 minute in order to obtain rest tremor data. After obtaining the rest tremor data, the person is requested to alternately touch his or her nose and the fingertip of a person located directly in front of them for a period of 1 minute in order to obtain kinetic tremor data. During the above time intervals, the actigraph 80 generates an analog movement signal that is representative of the movement of the patient over the collection period, digitizes the analog movement signal by sampling the analog signal at a predetermined sampling rate (e.g. 27 Hz), and stores the digital samples in a memory of the belt-worn unit 99. Accordingly, after the collection period is completed, the belt-worn unit 99 may be placed in the interface unit 84 so that the computer 83 may download the 12-bit digital samples that are representative of movement of the patient.

The above data collection process is repeated for each person of each group in order to obtain tremor data for each person of each group. In an exemplary embodiment, the computer 83 stores the downloaded digital samples for each person in a separate file. Accordingly, as a result of repeating the above data collection process for each person, the computer 83 obtains a first set of data files corresponding to people known to have Parkinson's disease, a second set of data files corresponding to people known to have essential tremor, and a third set of data files corresponding to people known to exhibit normal tremor characteristics.

In step 604, the computer 83 generates a training pattern set $TRAIN_{SET}$ and a test pattern set $TEST_{SET}$ from the obtained movement data obtained from the groups of people having known characteristics. In particular, the computer 83 in an exemplary embodiment utilizes a subset of the data files in order to generate the training pattern set $TRAIN_{SET}$ and the remaining data files in order to generate the test pattern set $TEST_{SET}$. Typically, fewer files are delegated to the creation of the test pattern set than the training pattern set; however, there is no requirement that this be the case. For example, the computer 83 for each group of data files may delegate 7 data files out of every 10 data files to the creation of the training pattern set $TRAIN_{SET}$ and use the remaining data files for the creation of the test pattern set $TEST_{SET}$.

The computer 83 then creates the training pattern set $TRAIN_{SET}$ by generating a separate input pattern $A_k$ and expected output pattern $B_K$ for each of the data files delegated to the training pattern set $TRAIN_{SET}$. Similarly, the computer 83 creates the test pattern set $TEST_{SET}$ by generating a separate input pattern $A_k$ and expected output pattern $B_K$ for each of the data files delegated to the test pattern set $TEST_{SET}$. More specifically, the computer 83 extracts characteristics from each data file in the same manner as the preprocessor 30 extracted characteristics from the collected movement data in step 404 of FIG. 4, and creates an input pattern $A_k$ from the extracted characteristics in the same manner as the preprocessor 30 created an input pattern in step 406 of FIG. 4.

The computer 83 then finishes the creation of the training pattern set $TRAIN_{SET}$ and the test pattern set $TEST_{SET}$ by associating an expected output pattern $B_k$ to each generated input pattern $A_k$. More specifically, if the input pattern $A_k$ was generated from a data file corresponding to a person known to have Parkinson's disease, then the computer 83 associates an expected output pattern $B_k$ to the input pattern $A_k$ which indicates that the person has Parkinson's disease. Similarly, if the input pattern $A_k$ was generated from a data file corresponding to a person known to have essential tremor, then the computer 83 associates an expected output pattern $B_k$ to the input pattern $A_k$ which indicates that the person has essential tremor. Furthermore, if the input pattern $A_k$ was generated from a data file corresponding to a person known to exhibit normal tremor characteristics, then the computer 83 associates an expected output pattern $B_k$ to the input pattern $A_k$ which indicates that the person exhibits normal tremor characteristics. In an exemplary embodiment, the computer 83 associates a first output pattern $B_K$ of 100 to Parkinson's disease, a second output $B_K$ of 010 to essential tremor, and a third output $B_K$ of 001 to normal tremor characteristics.

The computer 83 in step 606 then stores the input patterns $A_k$ and associated expected output pattern $B_k$ for each data file in either a training pattern file or a test pattern file.

Accordingly, the computer 83 obtains a training pattern file that includes the training pattern set $TRAIN_{SET}$ and a test pattern file that includes the test pattern set $TEST_{SET}$ which may be used to train and test the computational intelligence system 50 of the analysis system 10.

Exemplary Training Mechanism

Referring back to FIG. 1, there is depicted a training mechanism 60, a training pattern set 70, and a test pattern set 75. In general, the training mechanism 60 is operable to train the computational intelligence system 50 to classify movement based upon a predetermined group of neurological disorder classifications and test that the trained computational intelligence system 50 satisfies a threshold level of accuracy. To this end, the training mechanism 60 during a training phase essentially evolves parameters of the computational intelligence system 50 based upon the input patterns $A_k$ and expected output patterns $B_k$ of the training pattern set 70. Moreover, the training mechanism 60 during a testing phase essentially computes a fitness value for the trained computational intelligence system 50 based upon (i) output patterns $Z_k$ generated in response to the trained computational intelligence system 50 processing input patterns $A_k$ of the test pattern set 75, and (ii) expected output patterns $B_k$ of the test pattern set 75.

An exemplary training mechanism 60 for training a neural network implementation of the computational intelligence system 50 with particle swarm optimization is described in detail below. However, it should be appreciated that other training mechanisms such as error back-propagation, genetic algorithms, and evolutionary algorithms may be used to train the computational intelligence system 50 based upon the training patterns set 70.

Figure 7:
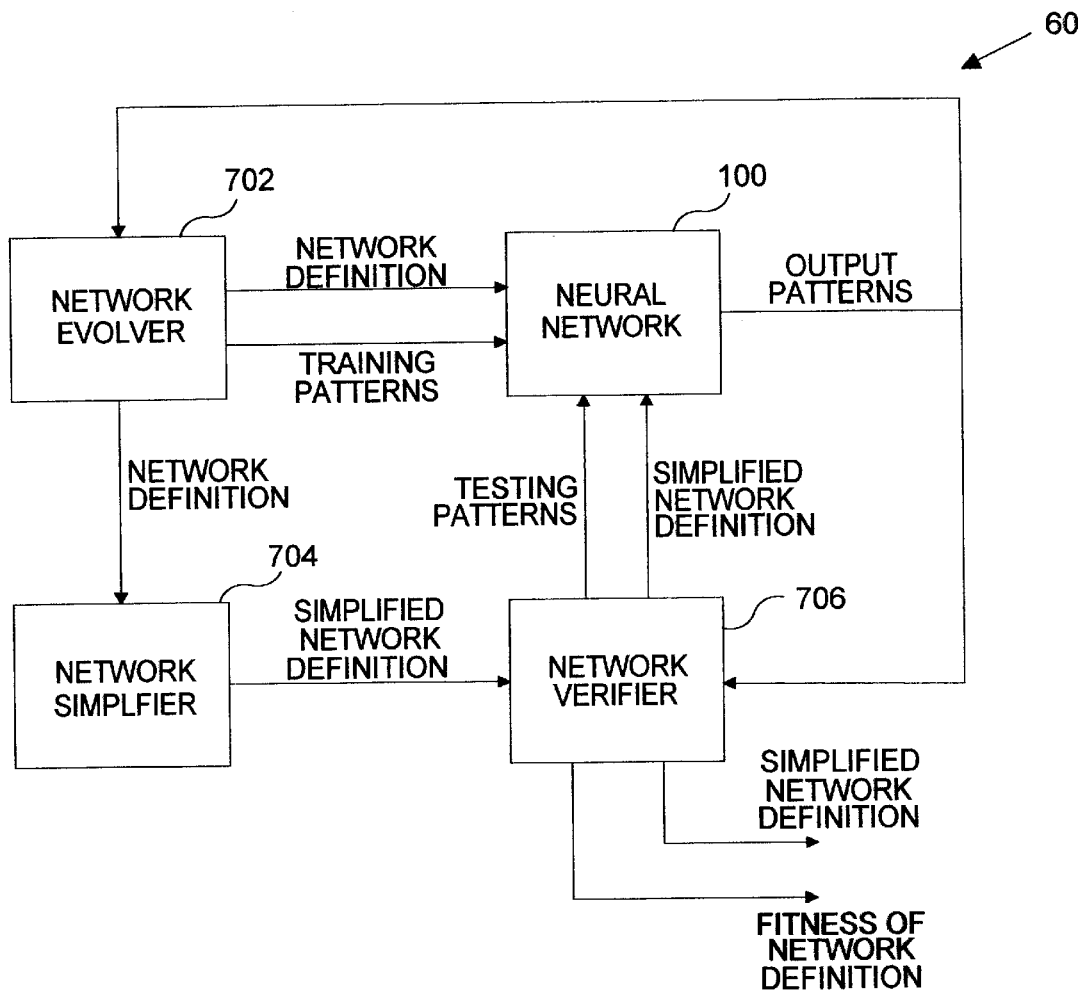
FIG. 7 shows a block diagram of an exemplary training mechanism suitable for training and testing the computational analysis system of FIG. 1.

Shown in greater detail in FIG. 7 is an exemplary training mechanism 60 of the analysis system 10 which defines and/or evolves weighted connection matrices W and U, activation functions F, and processing element layers $F_x$, $F_y$, and $F_z$ of the exemplary neural network 100 in order to obtain a computational intelligence system 50 trained to classify movement based upon input patterns $A_k$ and a group of predetermined neurological classifications. As depicted, the exemplary training mechanism 60 includes a network evolver 702, a network simplifier 704, and a network verifier 706. In general, the network evolver 702 is operable to (i) define an initial neural network architecture for the neural network 100, and (ii) continually adjust the architecture of the neural network 100 until the network evolver 702 obtains a definition for the neural network 100 that meets predefined criteria. More specifically, the network evolver 702 in an exemplary embodiment is operable to (i) apply input patterns $A_k$ of a training pattern set $TRAIN_{SET}$ to the input layer $F_x$ of the neural network 100, and (ii) adjust parameters of the neural network 100 based upon output patterns $Z_k$ generated by the neural network 100 in response to the input patterns $A_k$. As will be explained in more detail in reference to FIGS. 8A–8B, the network evolver 702 in an exemplary embodiment includes a particle swarm optimizer which is operable to adjust parameters of the neural network 100 in such a manner so as to achieve a trained neural network 100 that generates appropriate output patterns $Z_k$ in response to processing input patterns $A_k$.

The network simplifier 704 of the exemplary training mechanism 60 is generally operable to simplify the configuration of the neural network 100. As will be explained in more detail with reference to the network simplification method 900 of FIG. 9, the network simplifier 704 in an exemplary embodiment is operable to (i) receive a definition for the neural network 100 from the network evolver 702, (ii) redefine certain processing elements of the neural network 100 such that the processing element implements a simpler activation function, and (iii) remove unnecessary processing elements from the definition of the neural network 100.

Finally, the network verifier 706 of the exemplary training mechanism 60 is generally operable to verify the accuracy of the obtained simplified network definition for the neural network 100. More specifically, the network verifier 706 in an exemplary embodiment is operable to (i) apply input patterns $A_k$ of a test pattern set $TEST_{SET}$ to the input layer $F_x$ of the simplified definition of the neural network 100, and (ii) generate a fitness value that is indicative of how well the trained neural network 100 as defined by obtained simplified definition is able to produce appropriate output patterns $Z_k$ in response to processing input patterns $A_k$. In an exemplary embodiment, the network verifier 706 generates the fitness value for the trained neural network by calculating an average sum-squared error between the generated output patterns $Z_k$ and expected patterns $B_k$ of the test pattern set $TEST_{SET}$. (See, below equation (8) for details on performing an average sum-squared error calculation.)

From the produced fitness value for the simplified network definition, the exemplary training mechanism 60 is operable to determine whether the neural network 100 has been successfully trained. In particular, the exemplary training mechanism 60 in an exemplary embodiment determines that the neural network 100 has been successfully trained if the fitness value (e.g. average sum-squared error) for the simplified definition has a predetermined relationship to (e.g. less than) a fitness threshold value FITTHR (e.g. 0.01).

Figure 8A:
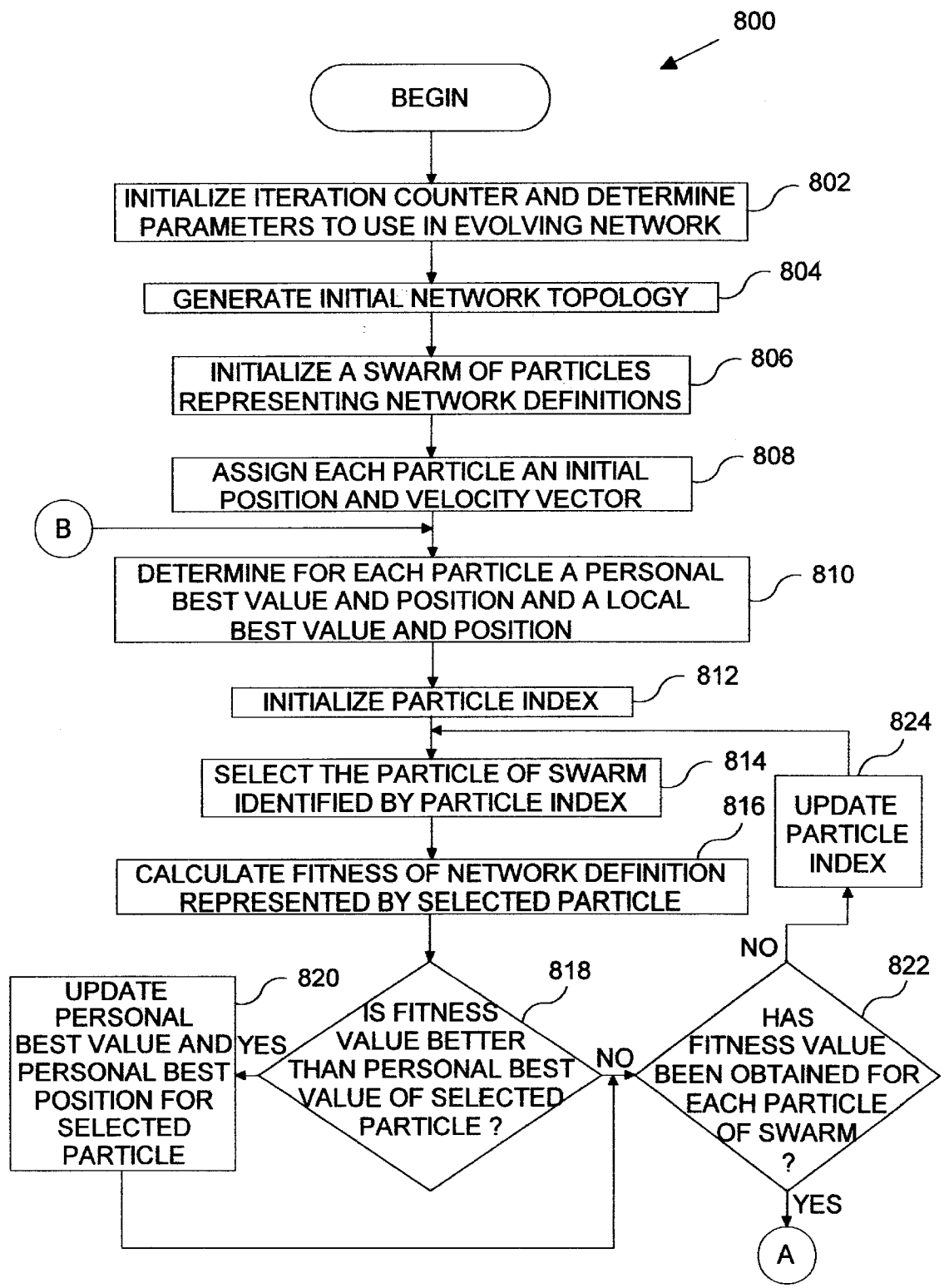
FIGS. 8A–8B show a flowchart of a network evolution method implemented by the exemplary training mechanism of FIG. 7.
Figure 8B:
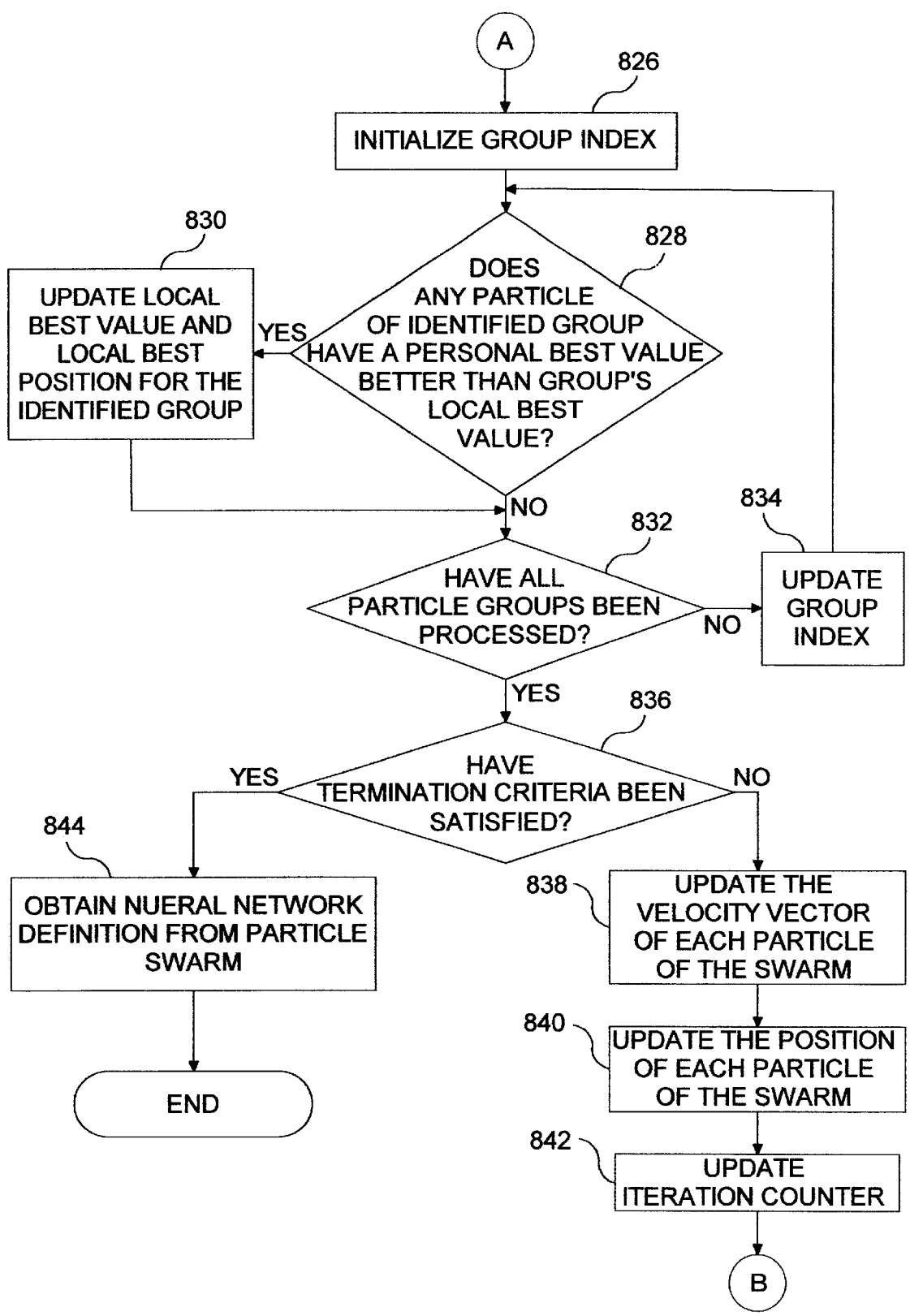

FIGS. 8A–8B show a flowchart of a network evolution method 800 that illustrates in detail the operation of the network evolver 702 of the exemplary training mechanism 60. As illustrated in FIG. 8A–8B, the network evolver 702 begins in step 802 by initializing an iteration counter ITER and determining various parameters to be used in evolving the neural network 100. More specifically, the network evolver 702 in an exemplary embodiment initializes the iteration counter ITER by setting the iteration counter to a value of 1.

Moreover, the network evolver 702 in an exemplary embodiment obtains various parameter values from a configuration file that define (i) a number of particles P# (e.g. 20) for a particle swarm S, (ii) a maximum particle velocity value $V_{MAX}$ (e.g. 10.0), (iii) a maximum position value $POS_{MAX}$ (e.g. 10.0), (iv) a dynamic initial lower limit value $LOWER_0$ (e.g. −0.5), (v) a dynamic initial upper limit value $UPPER_0$ (e.g. 0.5), (vi) a starting inertia weight $wi_0$ (e.g. 0.9), (vii) a slope upper limit $SLOPE_{ULIM}$ (e.g. 90), an error cutoff $E_{CUT}$ (e.g. 0.025), (vii) a maximum number of iterations $ITER_{MAX}$ (e.g. 1000), a training pattern set $TRAIN_{SET}$ (e.g. a file name of a file which includes training pairs of input patterns $A_k$ and corresponding expected output patterns $B_k$), a number of pattern pairs PAT# in the training pattern set $TRAIN_{SET}$ (e.g. 800), a test pattern set $TEST_{SET}$ (e.g. a file name of a file which includes testing pairs of input patterns $A_k$ and corresponding expected output patterns $B_k$), and a number of pattern pairs TPAT# in the test pattern set $TEST_{SET}$ (e.g. 500).

After obtaining the above parameters, the network evolver 702 in step 804 generates an initial topology for the neural network 100. More specifically, the network evolver 702 in an exemplary embodiment defines an appropriate three layer, fully connected, feed-forward network topology for the neural network 100. (See FIG. 5.) To this end, the network evolver 702 determines the number p of output signals $b_{jk}$ that each expected output pattern $B_k$ includes, and the number n of input signals and that each input pattern $A_k$ includes. From this information, the network evolver 702 defines an initial topology for the neural network 100 that includes (i) an input layer $F_x$ having a bias processing element $PEx_0$ and n input processing elements $PEx_h$, (ii) an output layer $F_z$ having p output processing elements $PEz_j$, and (iii) a hidden layer $F_y$ having a bias processing element $PEy_0$ and q hidden processing elements $PEy_i$.

A suitable number q of hidden processing elements can vary widely according to the application and bears a relationship to the number of statistically significant factors that exist in the input data. If there are too few hidden processing elements $PEy_i$, the network evolver 702 will probably fail to train the neural network 100. If there are just barely enough, the network evolver 702 may successfully train the neural network 100, but the resulting neural network 100 may fail to generate appropriate output patterns $Z_k$ for input patterns $A_k$ that were not part of the training pattern set $TRAIN_{SET}$. Moreover, the resulting neural network 100 will probably not handle noisy data well. Conversely, if there are too many hidden processing elements $PEy_i$, the resulting neural network 100 probably will not generalize very well. In other words, the resulting neural network 100 probably will not generate appropriate output patterns $Z_k$ for input patterns $A_k$ that were not part of the training pattern set $TRAIN_{SET}$.

Accordingly, the neural network may need to be trained several different times with different values of q until a suitable number q of hidden processing elements $PEy_i$ is found. A suitable number q of hidden processing elements $PEy_i$, however, may often be obtained by taking the square root of the number n of input processing elements $PEx_h$ squared plus the number p of output processing elements squared $PEz_j$ plus a few additional processing elements. This relationship for q is represented mathematically by the following equation (7):

$$q = \text{ceil}(\sqrt{n^2 + p^2}) + o \tag{7}$$

where n represents the number of input processing elements $PEx_h$, p represents the number of output processing elements $PEz_j$, ceil( ) represents a ceiling function which rounds a non-integer number up to the next integer number, and o represents a small integer with respect to $\text{ceil}(\sqrt{n^2 + p^2})$.

In an exemplary embodiment of the present invention, the values n, q, and p are supplied by a user via a configuration file that contains appropriate values for n, q, and p as well as the above discussed parameters. However, it should be appreciated that a user may alternatively supply the values n, q, and p as well as the above discussed parameters via an input device such as a mouse or a keyboard. Accordingly, the network evolver 702 in step 804 may determine appropriate values for n, q and p based upon (i) the input patterns $A_k$ and output pattern $B_k$ of the training pattern set $TRAIN_{SET}$, and/or (ii) user supplied parameters received via an input device and/or configuration file.

After defining an initial network topology for the neural network 100, the network evolver 702 in step 806 initializes a swarm S of particles $P_0, P_1, \ldots P_{P\#}$ that represent P# possible definitions for the neural network 100. More specifically, the network evolver 702 defines for each particle $P_x$ of the swarm S, (i) a position $POS_x$ in D-dimensional hyperspace, and a velocity vector $V_x$ through the D-dimensional hyperspace. More specifically, the network evolver 702 defines the D-dimensional hyperspace for the neural network 100 such that each dimension of the D-dimensional hyperspace represents a weighted connection $w_{hi}$ of the weighted connections matrix W, a weighted connection $u_{ij}$ of the weighted connections matrix U, a slope factor as of $\alpha_i$ slope vector A, or a slope factor $\beta_j$ of a slope vector B.

For example, if the neural network 100 is initially defined to include an (i) input layer $F_x$ having a bias processing element $PEx_0$ and two input processing elements $PEx_1$ and $PEx_2$, a hidden layer $F_y$ having a bias processing element $PEy_0$ and four hidden processing elements $PEy_1, PEy_2, \ldots$ and $PEy_4$, and an output layer $F_z$ having a single output processing element $PEz_1$, then the neural network 100 would have a weighted connections matrix W consisting of 12 weighted connections $w_{10}, w_{20}, \ldots w_{40}, w_{11}, w_{21}, \ldots w_{41}, w_{12}, w_{22}, \ldots w_{42}$, a weighted connections matrix U consisting of 5 weighted connections $u_{10}, u_{11}, \ldots u_{14}$, a slope vector A consisting of 4 slope factors $\alpha_1, \alpha_2, \ldots \alpha_4$, and a slope vector B consisting of 1 slope factor $\beta_1$. Therefore, the network evolver 702 in this example, would define a 22-dimensional hyperspace in which each position in the 22-dimensional hyperspace represents a possible solution for the 12 weighted connections of the weighted connections matrix W, the 5 weighted connections of the weighted connection matrix U, the 4 slope factors of the slope vector A, and the 1 slope factor of the slope vector B.

In an exemplary embodiment, the network evolver 702 in step 808 randomly assigns each particle $P_x$ of the particle swarm S an initial position $POS_x$ and velocity vector $V_x$. More specifically, the network evolver 702 randomly assigns the initial positions $POS_1, POS_2, \ldots POS_{P\#}$ of the particles $P_1, P_2, \ldots P_{p}\#$ such that the weight connections $w_{hi}$ and $u_{ij}$ represented by the positions $POS_1, POS_2, \ldots POS_{P\#}$ are between the initial lower limit $LOWER_0$ and initial upper limit $UPPER_0$. Moreover, the network evolver 702 assigns the initial positions $POS_1, POS_2, \ldots POS_{P\#}$ of the particles $P_1, P_2, \ldots P_{P\#}$ such that the slope factors $\alpha_i$ and $\beta_j$ are initially equal to 1. Furthermore, the network evolver randomly assigns the D-dimensional velocity vectors $V_1, V_2, \ldots V_{P\#}$ of the particles $P_1, P_2, \ldots P_{P\#}$ such that each dimensional velocity component $V_{x1}, V_{x2}, V_{xD}$ of a velocity vector $V_x$ is between the initial lower limit $LOWER_0$ and the initial upper limit $UPPER_0$.

After initializing the positions $POS_1, POS_2, \ldots POS_{P\#}$ of the particles $P_1, P_2, \ldots P_{P\#}$, the network evolver 702 in step 810 determines a personal best value $PBEST_x$, a personal best position $PBESTX_x$, a local best value $LBEST_x$, and a local best position $LBESTX_x$ for each particle of the particles $P_1, P_2, \ldots P_{P\#}$. More specifically, each personal best value $PBEST_x$ represents the corresponding best definition obtained by the particle $P_x$ for the neural network 100, and each personal best position $PBESTX_x$ represents the position in hyperspace where the particle $P_x$ obtained its corresponding particle best value $PBEST_x$. Similarly, each local best value $LBEST_x$ represents the corresponding best definition obtained by a particle group $PG_x$ that includes particles $P_{x-L}, \ldots P_{x-1}, P_x, P_{x+1}, \ldots P_{x+L}$, and each local best position $LBESTX_x$ represents the position in hyperspace where the particle group $PG_x$ obtained its corresponding local best value $LBEST_x$.

In an exemplary embodiment, the particle groups $PG_1, PG_2, \ldots PG_{P\#}$ are defined in a circular array fashion based upon a local neighbor parameter L. More specifically, if the local neighbor parameter L is equal to 2 and the number of particles is equal to 20, then the first particle group $PG_1$ would include particles $P_{19}, P_{20}, P_1, P_2$, and $P_3$ and the second particle group $PG_2$ would include the particles $P_{20}, P_1, P_2, P_3$, and $P_4$. It should be appreciated by those skilled in the art that if the local neighbor parameter L is equal to or greater than one-half the number of particles P#, then a single local best value LBEST and corresponding local best position LBESTX may be used since all of the particle groups $PG_1$, $PG_2$, ... $PG_{P\#}$ would include every particle $P_1$, $P_2$, ... $P_{P\#}$ of the particle swarm S. This special case is referred to as a global version of the particle swarm optimizer implemented by the network evolver 702. Moreover, the single local best value LBEST and corresponding local best position LBESTX in this special case are referred to as the global best value GBEST and the global best position GBESTX, respectively.

It has been found that the larger the local neighbor parameter L becomes the quicker (i.e. less iterations) on average the particle swarm optimizer of the network evolver 702 converges to an optimum. However, as the local neighbor parameter L becomes larger, the particle swarm optimizer of the network evolver 702 is more likely to converge on a local optimum instead of a global optimum. In other words, as the local neighbor parameter L becomes larger, the more likely the particle swarm optimizer of the network evolver 702 will fail to obtain a definition for the neural network 100 that achieves a desired level of performance. Accordingly, in an exemplary embodiment, the network evolver 702 utilizes a local neighbor parameter L of 2 which has been found to cause the particle swarm optimizer to converge on a global optimum as opposed to a local optimum at highly successful rate.

In order to determine a particle best value $PBEST_x$ and a particle best position $PBESTX_x$ for each particle $P_x$ of the particle swarm S, the network evolver 702 computes a fitness value $FV_x$ for each definition of the neural network 100 as defined by the particle positions $POS_1$, $POS_2$, ... $POS_{P\#}$. More specifically, the network evolver 702 in an exemplary embodiment calculates a fitness value $FV_x$ for each particle $P_x$ based upon a fitness function FIT( ) of (i) the output patterns $Z_1$, $Z_2$, $Z_{PAT\#}$ generated in response to propagating the input patterns $A_1$, $A_2$, ... $A_{PAT\#}$ of the training pattern set $TRAIN_{SET}$ through the neural network 100 as defined by the selected particle $P_x$, and (ii) the corresponding expected output patterns $B_1$, $B_2$, ... $B_{PAT\#}$ of the training pattern set $TRAIN_{SET}$. In an exemplary embodiment of the present invention, the network evolver 702 calculates the fitness value $FV_x$ of a particle $P_x$ based upon the following fitness function FIT( ) which computes the average sum-squared error between the output patterns $Z_1$, $Z_2$, ... $Z_{PAT\#}$ and the expected output patterns $B_1$, $B_2$, ... $B_{PAT\#}$:

$$FV_x = FIT(B, Z) = \frac{0.5 \sum_{k=1}^{PAT\#} \sum_{j=1}^{q} (b_{kj} - z_{kj})^2}{PAT\#} \quad (8)$$

where q represents the number of output processing elements of the neural network output layer $F_z$, $z_{kj}$ represents the output signal of the output processing element $PEz_j$ in response to the input pattern $A_k$ being applied to the neural network input layer $F_x$, $b_{kj}$ represents the corresponding expected output signal of the output processing element $PEz_j$, and PAT# represents the number of patterns of the training pattern set $TRAIN_{SET}$.

To this end of generating fitness values $FV_1$, $FV_2$, $FV_{P\#}$ for the particles $P_1$, $P_2$, $P_{P\#}$, the network evolver 702 in step 812 initializes a particle index N to a value of 1 in order to cause the particle index N to identify the first particle $P_1$ of the particle swarm S. The network evolver 702 then in step 814 selects the particle $P_N$ identified by the particle index N.

After selecting the particle $P_N$ identified by the particle index N, the network evolver 702 in step 816 calculates a fitness value $FV_N$ for the particle definition of the neural network 100 via the above fitness function FIT( ). In particular, the network evolver 702 in an exemplary embodiment generates output patterns $Z_1$, $Z_2$, ... $Z_{PAT\#}$ in response to applying the input patterns $A_1$, $A_2$, ... $A_{PAT\#}$ of the training pattern set $TRAIN_{SET}$ to a definition of the neural network 100 as defined by the position $POS_N$ of the selected particle $P_N$. More specifically, the network evolver 702 generates the output patterns $Z_1$, $Z_2$, ... $Z_{PAT\#}$ based upon a definition of the neural network 100 in which the neural network 100 has a weighted connections matrix W, a weighted connections matrix U, a slope vector A, and a slope vector B as defined by the position $POS_N$ of the selected particle $P_N$. Moreover, the network evolver 702, in the exemplary embodiment, generates a fitness value $FV_N$ for the selected particle $P_N$ based upon above equation (8) which causes the network evolver 702 to calculate the average sum-squared error between the generated output patterns $Z_1$, $Z_2$, ... $Z_{PAT\#}$ and the expected output patterns $B_1$, $B_2$, ... $B_{PAT\#}$ of the training pattern set $TRAIN_{SET}$.

After obtaining the fitness value $FV_N$ for the selected particle $P_N$, the network evolver 702 in step 818 determines whether the personal best value $PBEST_N$ and personal best position $PBESTX_N$ for the selected particle $P_N$ need to be updated. To this end, the network evolver 702 determines whether the obtained fitness value $FV_N$ for the selected particle $P_N$ is better than the current personal best value $PBEST_N$ for the selected particle $P_N$. If the obtained fitness value $FV_N$ for the selected particle $P_N$ is better than the current personal best value $PBEST_N$ for the selected particle $P_N$, then the network evolver 702 proceeds to step 820 in order to update the personal best value $PBEST_N$ and personal best position $PBESTX_N$ for the selected particle $P_N$. Otherwise, if the obtained fitness value $FV_N$ for the selected particle $P_N$ is not better than the current personal best value $PBEST_N$ for the selected particle $P_N$, then the network evolver 702 proceeds to step 822 in order to determine whether a fitness value $FV_x$ has been obtained for each particle $P_x$.

In an exemplary embodiment, the network evolver 702 attempts to minimize the fitness value $FV_x$ (i.e. average sum-squared error) for the neural network 100. Accordingly, in the exemplary embodiment, the network evolver 702 determines that an obtained fitness value $FV_N$ is better than personal best value $PBEST_N$ if the fitness value $FV_N$ is less than the personal best value $PBEST_N$. However, it should be appreciated that the fitness function FIT( ) may be defined in such a way that the network evolver 702 needs to maximize the fitness values $FV_x$ in order to properly train the neural network 100. Accordingly, in such a maximization environment, the network evolver 702 would determine that the a fitness value $FV_N$ is better than a personal best value $PBEST_N$ if the fitness value $FV_N$ is greater than the personal best value $PBEST_N$. Moreover, it should be appreciated that the fitness function of equation (8) is merely exemplary and that other fitness functions may be used.

After determining that the fitness value $FV_N$ is better than the personal best value $PBEST_N$ for the selected particle $P_N$, the network evolver 702 in step 820 updates the personal best value $PBEST_N$ and the personal best position $PBESTX_N$ for the selected particle $P_N$. More specifically, the network evolver 702 sets the personal best value $PBEST_N$ equal to the calculated fitness value $FV_N$ for the selected particle $P_N$. Moreover, the network evolver 702 sets the personal best position $PBEST_N$ equal to the position POSN of the selected particle $P_N$.

It should be noted that in an exemplary embodiment, the personal best values $PBEST_x$ are initially set to zero so that network evolver 702 during the first iteration through the network evolution method 800 (i.e. iteration counter ITER equal to 1) will update the personal best values $PBEST_N$ with the calculated fitness value $FV_N$ for the selected particle $P_N$.

In step 822, the network evolver 702 determines whether a fitness value $FV_x$ has been obtained for each particle $P_1$, $P_2$, ... $P_{P\#}$ of the particle swarm S. If the network evolver 702 determines that a fitness value $FV_x$ has been obtained for each particle $P_1, P_2, \ldots P_{P\#}$ of the particle swarm S, then the network evolver 702 proceeds to step 826 of the network evolution method 800. However, if the network evolver 702 determines that a fitness value $FV_x$ has not been obtained for each particle $P_1, P_2, \ldots P_{P\#}$ of the particle swarm S, then the network evolver 702 proceeds to step 824 of the network evolution method 800. In an exemplary embodiment of the present invention, the network evolver 702 determines that a fitness value $FV_x$ has been obtained for each particle $P_1$, $P_2, \ldots P_{P\#}$ of the particle swarm S if the particle index N is greater than the number of particles P# included in the particle swarm S.

After determining that a fitness value $FV_x$ has not been obtained for each particle $P_1, P_2, \ldots P_{P\#}$, the network evolver 702 in step 824 updates the particle index N and returns to step 814 in order to select the particle $P_N$ identified by the updated particle index N and obtain a fitness value $FV_N$ for the newly selected particle $P_N$. In an exemplary embodiment, the network evolver 702 updates the particle index N by incrementing the particle index N by a value of 1.

After determining that a fitness value $FV_x$ has been obtained for each particle $P_1, P_2, \ldots P_{P\#}$, the network evolver 702 updates the local best value $LBEST_x$ and local best position $LBESTX_x$ for each particle $P_1, P_2, \ldots P_{P\#}$. To this end, the network evolver 702 in step 826 initializes a group index M to a value of 1 in order to obtain a group index M that identifies a first particle group $PG_1$. Then, the network evolver 702 in step 828 determines whether any particle $P_{M-L}, \ldots P_{M-1}, P_M, P_{M+1}, \ldots P_{M+L}$ of the identified group $PG_M$ has a personal best value $PBEST_x$ that is better than the current local best value $LBEST_M$ for the identified particle group $PG_M$. If any of the personal best values $PBEST_{M-L}, \ldots PBEST_{M-1}, PBEST_M, PBEST_{M+1}, \ldots PBEST_{M+L}$ of the identified group $PG_M$ is better than the current local best value $LBEST_M$ for the identified particle group $PG_M$, then the network evolver proceeds to step 830 in order to update the local best value $LBEST_M$ for the identified particle group $PG_M$. Otherwise, if none of the personal best values $PBEST_{M-L}, \ldots PBEST_{M-1}, PBEST_M, PBEST_{M+1}, \ldots PBEST_{M+L}$ of the identified group $PG_M$ are better than the current local best value $LBEST_M$ for the identified particle group $PG_M$, then the computer system proceeds to step 832 in order to determine whether all particle groups $PG_1, PG_2, \ldots PG_{P\#}$ have been processed.

After determining that at least one personal best value $PBEST_{M-L}, \ldots PBEST_{M-1}, PBEST_M, PBEST_{M+1}, \ldots PBEST_{M+L}$ of the identified group $PG_M$ is better than the current local best value $LBEST_M$, the network evolver 702 in step 830 updates the local best value $LBEST_M$ and the local best position $LBESTX_M$ for the identified particle group $PG_M$. More specifically, the network evolver 702 sets the local best value $LBEST_M$ equal to the best, personal best value $PBEST_B$ of the identified group $PG_M$. Moreover, the network evolver 702 sets the local best position $LBESTX_M$ equal to the personal best position $PBESTX_B$ associated with the best, personal best value $PBEST_B$ of the identified group $PG_M$.

It should be noted that in an exemplary embodiment, the local best values $LBEST_x$ are initially set to zero so that the network evolver 702 during the first iteration through the network evolution method 800 (i.e. iteration counter ITER equal to 1) will update the local best values $LBEST_x$ with one of the personal best values $PBEST_{M-L}, \ldots PBEST_{M-1}$, $PBEST_M, PBEST_{M+1}, \ldots PBEST_{M+L}$ of its respective particle group $PG_x$. In another exemplary embodiment, the network evolver 702 during the first iteration through the network evolution method 800 sets each $LBEST_x$ of a particle $P_x$ equal to its respective personal best value $PBEST_x$ in step 820. Under either exemplary embodiment, each local best value $LBEST_x$ should be equal to the best, personal best value $PBEST_{X-L}, \ldots PBEST_{X-1}, PBEST_X$, $PBEST_{X+1}, \ldots PBEST_{X+L}$ of its respective particle group $PG_x$ after the first iteration through the network evolution method 800.

In step 832, the network evolver 702 determines whether all of the particle groups $PG_1, PG_2, \ldots PG_{P\#}$ have been processed. If all of the particle groups $PG_1, PG_2, \ldots PG_{P\#}$ have been processed, then the network evolver 702 proceeds to step 836 in order to determine whether termination criteria have been satisfied. However, if all of the particle groups $PG_1, PG_2, \ldots PG_{P\#}$ have not been processed, then the network evolver 702 proceeds to step 834. In an exemplary embodiment, the network evolver 702 determines that all of the particle groups $PG_1, PG_2, \ldots PG_{P\#}$ have been processed if the particle group index M is greater than the number of particles P# of the swarm S.

In step 834, the network evolver 702 updates the particle group index M and returns to step 828 in order to process the next particle group $PG_M$. In an exemplary embodiment, the network evolver 702 updates the particle group index M by incrementing the particle group index M by a value of 1.

After processing all of the particle groups $PG_1, PG_2, \ldots PG_{P\#}$, the network evolver 702 in step 836 determines whether defined termination criteria have been satisfied. If the network evolver 702 determines that the defined termination criteria have been satisfied, then the network evolver 702 proceeds to step 844 in order define the weighted connections matrix W, the weighted connections matrix U, the slope vector A, and the slope vector B. However, if the network evolver 702 determines that the defined termination criteria have not been satisfied, then the network evolver 702 proceeds to step 838 in order to update the velocity vectors $V_1, V_2, \ldots V_{P\#}$ associated with the particles $P_1, P_2, \ldots P_{P\#}$.

In an exemplary embodiment of the present invention, the termination criteria are defined by a maximum number of iterations $ITER_{MAX}$ and an error cutoff $E_{CUT}$. More specifically, the network evolver 702 in an exemplary embodiment determines to terminate the network evolution method 800 in response to (i) the iteration counter ITER having a predetermined relationship to the maximum number of iterations $ITER_{MAX}$, or (ii) the best of the local best values $LBEST_1, LBEST_2, \ldots LBEST_{P\#}$ having a predetermined relationship to the desired error cutoff $E_{CUT}$. For example, in an exemplary embodiment which attempts to minimize the fitness values $FV_x$, the network evolver 702 may be implemented to terminate the network evolution method 800 if either (i) the iteration counter ITER is equal to the maximum number of iterations $ITER_{MAX}$, or (ii) the best of the local best values $LBEST_1, LBEST_2, \ldots LBEST_{P\#}$ is less than the desired error cutoff $E_{CUT}$.

In step 838, the network evolver 702 updates the velocity vector $V_x$ for each particle $P_x$ of the swarm S. More specifically, the network evolver 702 updates the velocity vector $V_x$ of a particle $P_x$ based upon (i) an inertia weight wi, (ii) the personal best position $PBESTX_x$ of the particle $P_x$, and (iii) the local best position $LBESTX_x$ for the particle group $PG_x$ to which the particle $P_x$ belongs. In an exemplary embodiment, the network evolver 702 updates each velocity component $v_{x1}, v_{x2}, \ldots v_{xD}$ of the velocity vector $V_x$ for a particle $P_x$ based upon the following velocity equation (9):

$$v_{xd}' = wi*v_{xd} + c_1*\text{rand}(\ )*(pbestx_{xd} - pos_{xd}) + c_2*\text{Rand}(\ )*(lbestx_{xd} - pos_{xd}) \quad (9)$$

In the above velocity equation (9), $v_x'$ represents an updated velocity component of the velocity vector $V_x$ in the $d^{th}$ dimension, $v_{xd}$ represents the current velocity component of the velocity vector $V_x$ in the $d^{th}$ dimension, wi represents the inertia weight parameter, and $c_1$ and $c_2$ represent acceleration constants. Moreover, rand( ) and Rand( ) represent random functions that each generate a random number in the range between 0 and 1. Furthermore, $pos_{xd}$ represents the position of the particle $P_x$ in the $d^{th}$ dimension, $pbestx_{xd}$ represents the position of the personal best value $PBEST_x$ in the $d^{th}$ dimension, and $lbestx_{xd}$ represents the position of the local best value $LBEST_x$ in the $d^{th}$ dimension.

The inertia weight parameter wi and the acceleration constants $c_1$ and $c_2$ may be used to control the tension in the system. Lower values (less than 1) for $c_1$ and $c_2$ tend to increase the time it takes for particles $P_x$ to arrive in the vicinity of their respective personal best values $PBEST_x$ and local best values $LBEST_x$, whereas higher values (greater than 1) for the acceleration constants $c_1$ and $c_2$ tend to allow particles $P_x$ to explore larger regions around their respective personal best values $PBEST_x$ and local best values $LBEST_x$. Similarly, high values for the inertia weight parameter wi tend to allow particles $P_x$ to roam farther from their respective personal best values $PBEST_x$ and local best values $LBEST_x$, whereas low values for the inertia weight parameter wi tend to restrict particles $P_x$ to regions nearer their respective personal best values $PBEST_x$ and local best values $LBEST_x$.

In an exemplary embodiment of the present invention, the network evolver 702 sets the acceleration constants equal to a value of 2. Moreover, the network evolver 702 decreases the inertia weight wi linearly over the defined maximum iterations $ITER_{MAX}$ from the initial inertia weight $wi_0$ to a final inertia weight such as 0.4. The advantage of adjusting the inertia weight wi from a high value of 0.9 to a low value of 0.4 is that the particles $P_1, P_2, \ldots P_{P\#}$ initially perform a more global exploration and move gradually toward a more local exploration.

Moreover, in an exemplary embodiment, the network evolver 702 clips the updated velocity components $v_{x1}', v_{x2}', \ldots v_{xD}'$ such that no updated velocity component $v_{xd}'$ is greater than the maximum velocity parameter $V_{MAX}$. For example, if the network evolver 702 obtains an updated velocity component $v_{xd}'$ equal to 11.3 and the maximum velocity parameter $V_{MAX}$ is set to 10.0, then the network evolver 702 would set the updated velocity component $v_{xd}'$ equal to 10.0 instead of 11.3.

After updating the velocity vector $V_x$ for each particle $P_x$ of the particle swarm S, the network evolver 702 in step 840 updates each position $POS_x$ of each particle $P_x$. In particular, the network evolver 702 updates each position component $pos_{x1}, pos_{x2}, \ldots pos_{xD}$ of each position $POS_x$ based upon the updated velocity vector $V_x$ for corresponding particle $P_x$. To this end, the network evolver 702 in an exemplary embodiment updates each position component $pos_{x1}, pos_{x2}, \ldots pos_{xD}$ of a particle position $POS_x$ based upon the following position equation (10).

$$pos_{xd}' = pos_{xd} + v_{xd}' \quad (10)$$

where $pos_{xd}$ represents the current position component of the particle position $POS_x$ in the $d^{th}$ dimension, $pos_{xd}'$ represents the updated position component of the particle position $POS_x$ in the $d^{th}$ dimension, and $v_{xd}'$ represents the updated velocity component for the particle $P_x$ in the $d^{th}$ dimension. Moreover, in an exemplary embodiment, the network evolver 702 clips the updated position components $pos_{x1}', pos_{x2}', \ldots pos_{xD}'$ such that no updated position component $pos_{xd}'$ is greater than the maximum position parameter $POS_{MAX}$. For example, if the network evolver 702 obtains an updated position component $pos_{xd}'$ equal to $-11.3$ and the maximum position parameter $POS_{MAX}$ is set to 10.0, then the network evolver 702 would set the updated position component $pos_{xd}'$ equal to $-10.0$ instead of $-11.3$. However, it should be appreciated that the network evolver 702 may also be implemented such that the updated positions components $pos_{x1}', pos_{x2}', \ldots pos_{xD}'$ are not limited to a specified range.

In step 842, the network evolver 702 updates the iteration counter ITER and returns to step 810 in order to process the updated particles $P_1, P_2, \ldots P_{P\#}$ of the particle swarm S. In particular, the network evolver 702 in an exemplary embodiment increments the iteration counter ITER by a value of 1 before returning to step 810.

After the termination criteria are satisfied, the network evolver 702 in step 844 obtains a neural network definition for the neural network 100 from the particle swarm S. More specifically, the network evolver 702 obtains the position in the D-dimensional hyperspace that achieved that best fitness value and uses this position to define the weighted connections matrix W, the weighted connections matrix U, the slope matrix A, and the slope matrix B of the neural network 100. To this end, the network evolver 702 in an exemplary embodiment (i) obtains the best, personal best position $PBESTX_B$ associated with the best of the personal best values $PBEST_1, PBEST_2, \ldots PBEST_{P\#}$, (ii) sets each weighted connection $w_{hi}$ of the weighted connections matrix W, each weighted connection $u_{ij}$ of the weighted connections matrix U, each slope factor $\alpha$ of the slope factor A, and each slope factor $\beta$ of the slope vector B equal to a respective position component $pbestx_{B1}, pbestx_{B2}, \ldots pbest_{BD}$ of the best, personal best position $PBESTX_B$.

Similarly, in another exemplary embodiment, the network evolver 702 (i) obtains the best, local best position $LBESTX_B$ associated with the best of the local best values $LBEST_1, LBEST_2, \ldots LBEST_{P\#}$, (ii) sets each weighted connection $w_{hi}$ of the weighted connections matrix W, each weighted connection $u_{ij}$ of the weighted connection matrix U, each slope factor $\alpha$ of the slope factor A, and each slope factor $\beta$ of the slope vector B equal to a respective position component $lbestx_{B1}, lbestx_{B2}, \ldots lbest_{BD}$ of the best, local best position $PBESTX_B$. It should be appreciated that either of the two exemplary embodiments should achieve the same results for the weighted connections matrix W, the weighted connections matrix U, the slope vector A, and the slope vector B.

Exemplary Network Simplification Method

Figure 9:
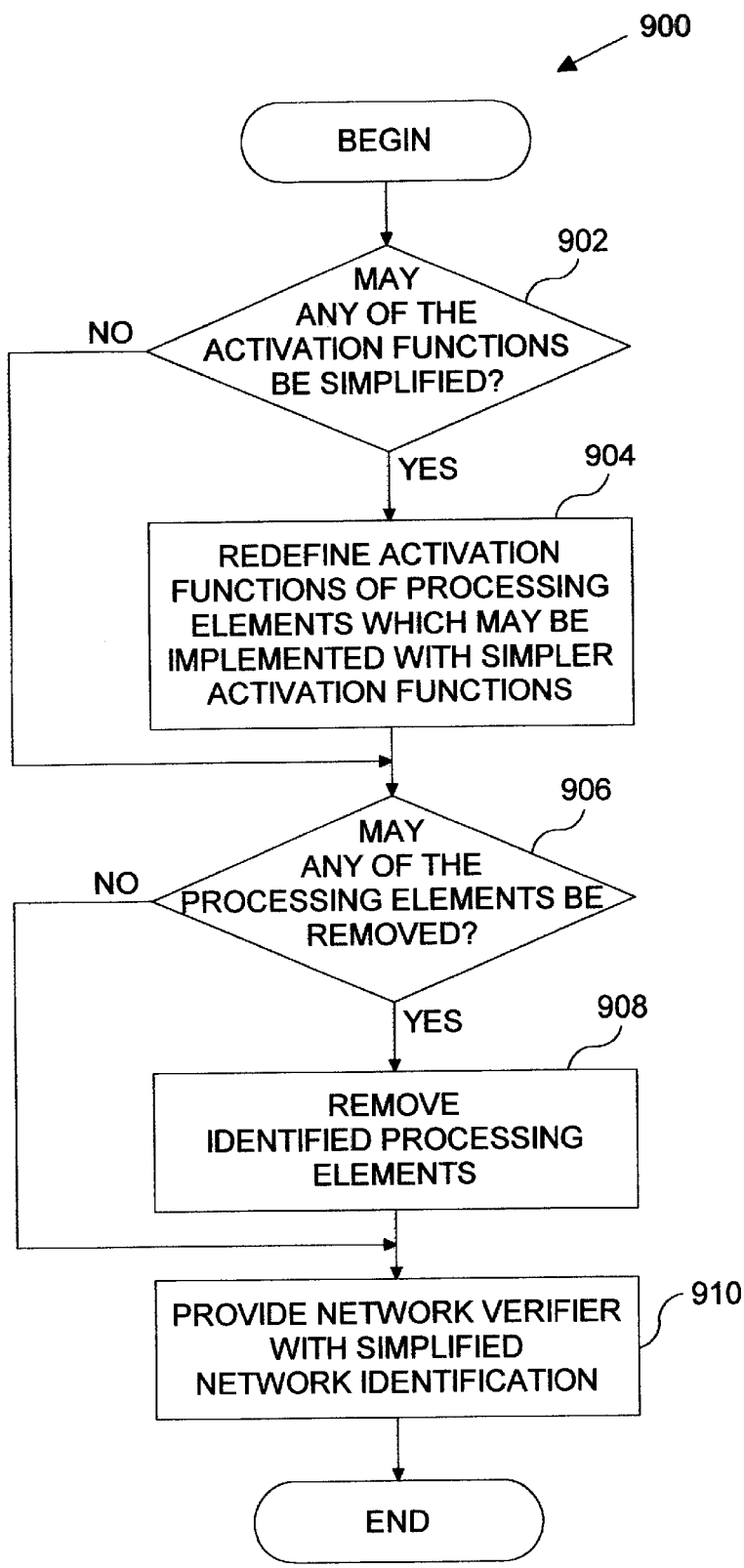
FIG. 9 shows a flowchart of a network simplification method implemented by the exemplary training mechanism of FIG. 7.

Referring now to FIG. 9, there is illustrated a flowchart of an network simplification method 900. In general, the network simplification method 900 when executed by the network simplifier 704 causes the network simplifier 704 to simplify a definition for the neural network 100 of the computation intelligence 50 in order to obtain a less complex definition of the neural network 100. More specifically, the network simplifier 704 in implementing the network simplification method 900 generally (i) removes unnecessary processing elements from the neural network 100, and/or (ii) replaces complex activation functions of certain processing elements with less computationally complex activation functions.

To this end, the network simplifier 704 in step 902 determines based upon the slope vector A and the slope vector B whether any of the activation functions of the hidden processing elements $PEy_1, PEy_2, \ldots PEy_q$ or the output processing elements $PEz_1, PEz_2, \ldots PEz_p$ may be simplified. In an exemplary embodiment, each hidden processing element $PEy_i$ is initially implemented with the sigmoid threshold function of equation (3) and each output processing element $PEz_j$ is initially implemented with the sigmoid threshold function of equation (6). As can be seen from equations (3) and (6), if the slope factors $\alpha$ and $\beta$ are positive and have a sufficiently large magnitude, the sigmoid activation function essentially becomes the following step threshold function (11):

$$f(x) = \begin{cases} 1 & \text{if } x \geq 0 \\ 0 & \text{if } x < 0 \end{cases} \quad (11)$$

Similarly, if the slope factors $\alpha$ and $\beta$ are negative and have a sufficiently large magnitude, the sigmoid threshold function essentially becomes the following step threshold function (12):

$$f(x) = \begin{cases} 1 & \text{if } x \leq 0 \\ 0 & \text{if } x > 0 \end{cases} \quad (12)$$

As a result of the above properties of the sigmoid threshold function, the network simplifier 704 in an exemplary embodiment determines that activation functions of the neural network 100 may be simplified if any of the slope factors $\alpha$ and $\beta$ of the slope vectors A and B has a magnitude greater than a slope upper limit $SLOPE_{ULIM}$. It has been found that a slope upper limit $SLOPE_{ULIM}$ as small as 10 often results in a simplified neural network 100 with minimal effect on the accuracy of the output patterns $Z_k$ generated by the neural network 100.

In step 904, the network simplifier 704 redefines the activation functions for those processing elements PE which may be implemented with a simpler activation function. In particular, for each hidden processing element $PEy_i$ with a positive slope factor $\alpha_i$ having a magnitude greater than the slope upper limit $SLOPE_{ULIM}$, the network simplifier 704 in an exemplary embodiment replaces the sigmoid threshold function of the hidden processing element $PEy_i$ with the step threshold function of equation (11). Moreover, for each hidden processing element $PEy_i$ with a negative slope factor $\alpha_i$ having a magnitude greater than the slope upper limit $SLOPE_{ULIM}$, the network simplifier 704 replaces the sigmoid threshold function of the hidden processing element $PEy_i$ with the step threshold function of equation (12). Similarly, for each output processing element $PEz_j$ with a positive slope factor $\beta_j$ having a magnitude greater than the slope upper limit $SLOPE_{ULIM}$, the network simplifier 704 in an exemplary embodiment replaces the sigmoid threshold function of the output processing element $PEz_j$ with the step threshold function of equation (11). Moreover, for each output processing element $PEz_j$ with a negative slope factor $\alpha_j$ having a magnitude greater than the sloe upper limit $SLOPE_{ULIM}$, the network simplifier 704 replaces the sigmoid threshold function of the output processing element $PEz_j$ with the step threshold function of equation (12).

The network simplifier 704 then in step 906 determines whether any of the hidden processing elements $PEy_1, PEy_2, \ldots PEy_q$ may be removed from the neural network 100. If the network simplifier 704 determines that at least one of the hidden processing elements $PEy_1, PEy_2, \ldots PEy_q$ may be removed from the neural network 100, then the network simplifier 704 proceeds to step 908. However, if the network simplifier 704 determines that none of the hidden processing elements $PEy_1, PEy_2, \ldots PEy_q$ may be removed from the neural network 100, then the network simplifier proceeds to step 910.

As stated above, each hidden processing elements $PEy_i$, of the neural network 100 in an exemplary embodiment is initially implemented with the sigmoid threshold function of equation (3). As can be seen from the sigmoid threshold function of equation (3), the output of the sigmoid threshold function is roughly equal to a constant value of 0.5 when the magnitude of the slope factor $\alpha$ is less than a slope lower limit $SLOPE_{LLIM}$. Accordingly, the network simplifier 704 in an exemplary embodiment determines that a hidden processing element $PEy_i$ may be removed from the neural network 100 if the slope factor c associated with the hidden processing element $PEy_i$ is less than the slope lower limit $SLOPE_{LLIM}$. Appropriate values for the slope lower limit $SLOPE_{LLIM}$ are dependent upon the application; however, the network simplifier 704 in an exemplary embodiment uses a lower slope limit $SLOPEL_{LIM}$ of 0.1 which may be sufficient for many different types of applications.

In step 908, the network simplifier 704 removes those hidden processing elements $PEy_i$ identified in step 906 as being appropriate for removal. To this end, for each hidden processing element $PEy_i$ with a slope factor $\alpha_i$ having a magnitude less than the slope lower limit $SLOPE_{LLIM}$, the network simplifier 704 (i) removes the identified hidden processing element $PEy_i$, (ii) removes the weighted connections vector $W_i$ from the weighted connections matrix W associated with the removed hidden processing element $PEy_i$, (iii) updates the biasing weight connections $u_{10}, u_{20}, u_{p0}$ in order to replicate the function of the removed hidden processing element $PEy_i$, and (iv) removes the weighted components $u_{1i}, u_{2i}, \ldots u_{pi}$ from the weighted connections matrix U associated with the removed hidden processing element $PEy_i$.

Figure 10:
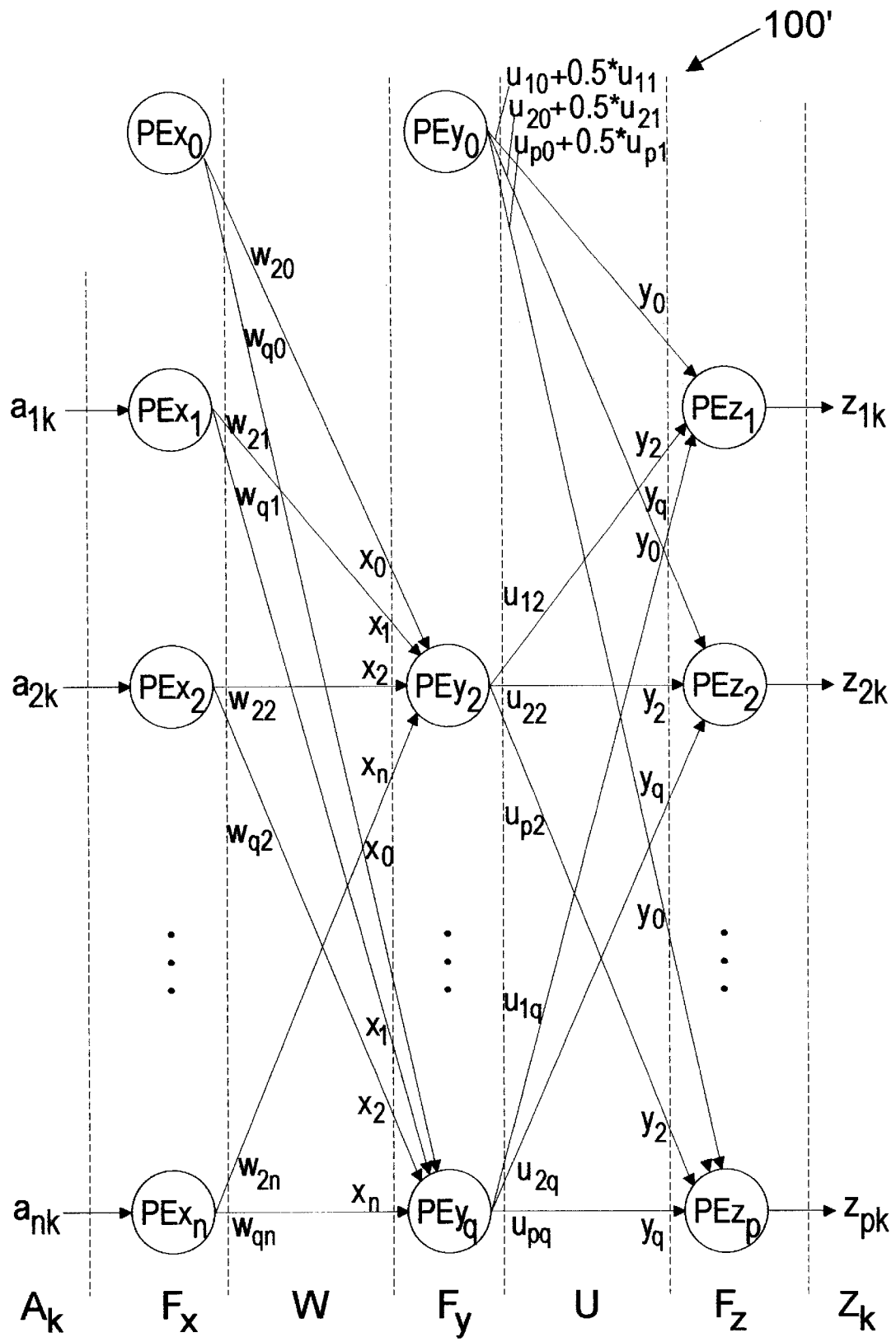
FIG. 10 illustrates the manner by which the network simplification method of FIG. 9 removes a processing element from the exemplary neural network of FIG. 5.

More specifically, since the removed hidden processing element $PEy_i$ essentially generated a constant output signal $y_i$ of 0.5, the removed hidden processing $PEy_i$ essentially affected each of the output processing elements $PEz_1, PEz_2, \ldots PEz_p$ by an amount of 0.5 times the respective weighted connections $u_{1i}, u_{2i}, \ldots u_{pi}$. Accordingly, the network simplifier 704 in an exemplary embodiment replicates the effect of the removed hidden processing element $PEy_i$ by increasing the biasing weighted connections $u_{10}, u_{20}, \ldots u_{p0}$ from the biasing processing element $PEy_0$ by 0.5 times the removed weight connections $u_{1i}, u_{2i}, \ldots u_{pi}$. The following equation (13) represents this update of the biasing weight connections $u_{10}, u_{20}, \ldots u_{p0}$:

$$u_{k0}' = u_{k0} + 0.5 * u_{ki} \quad (13)$$

where $u_{k0}'$ represents the updated $k^{th}$ weighted connection from the biasing processing element $PEy_0$, $u_{k0}$ represents the current $k^{th}$ weighted connection from the biasing processing element $PEy_0$, and $u_{ki}$ represents the $k^{th}$ weighted connection associated with the removed hidden processing element $PEy_i$. For example, FIG. 10 illustrates a simplified neural network 100' in which the hidden processing element $PEy_1$ has been removed from the neural network 100 of FIG. 5, and the biasing weighted connections $u_{10}, u_{20}, \ldots u_{p0}$ have been updated to replicate the effect of the removed hidden processing element $PEy_1$.

In step 910, the network simplifier 704 transfers the simplified definition of the neural network 100 to the network verifier 706. In particular, the network simplifier 704 transfers the obtained weighted connections matrix W, the weighted connections matrix U, the slope vector A, and the slope vector B to the network verifier 706. The network verifier 706 may then test the obtained simplified definition for the neural network 100 by applying test input patterns $A_k$ of the test pattern set $TEST_{SET}$, and calculating a fitness value for the simplified definition based upon generated output patterns $Z_k$ and expected output patterns $B_k$ of the test pattern set $TEST_{SET}$.

It should be appreciated by those skilled in the art that the above exemplary training mechanism 60 may be used to train neural networks having processing elements that utilize different activation functions. For example, the above exemplary training mechanism 60 may be used to evolve and simplify neural networks that utilize the threshold functions of below TABLE 1. More specifically, the network simplifier 706 may replace a processing element threshold function with the simpler threshold function if the slope factor α of the processing element meets the criteria of TABLE 1. Moreover, the network simplifier 706 may remove hidden layer processing elements of the neural network 100 if the simplified threshold function generates a constant output.

Figure 11:
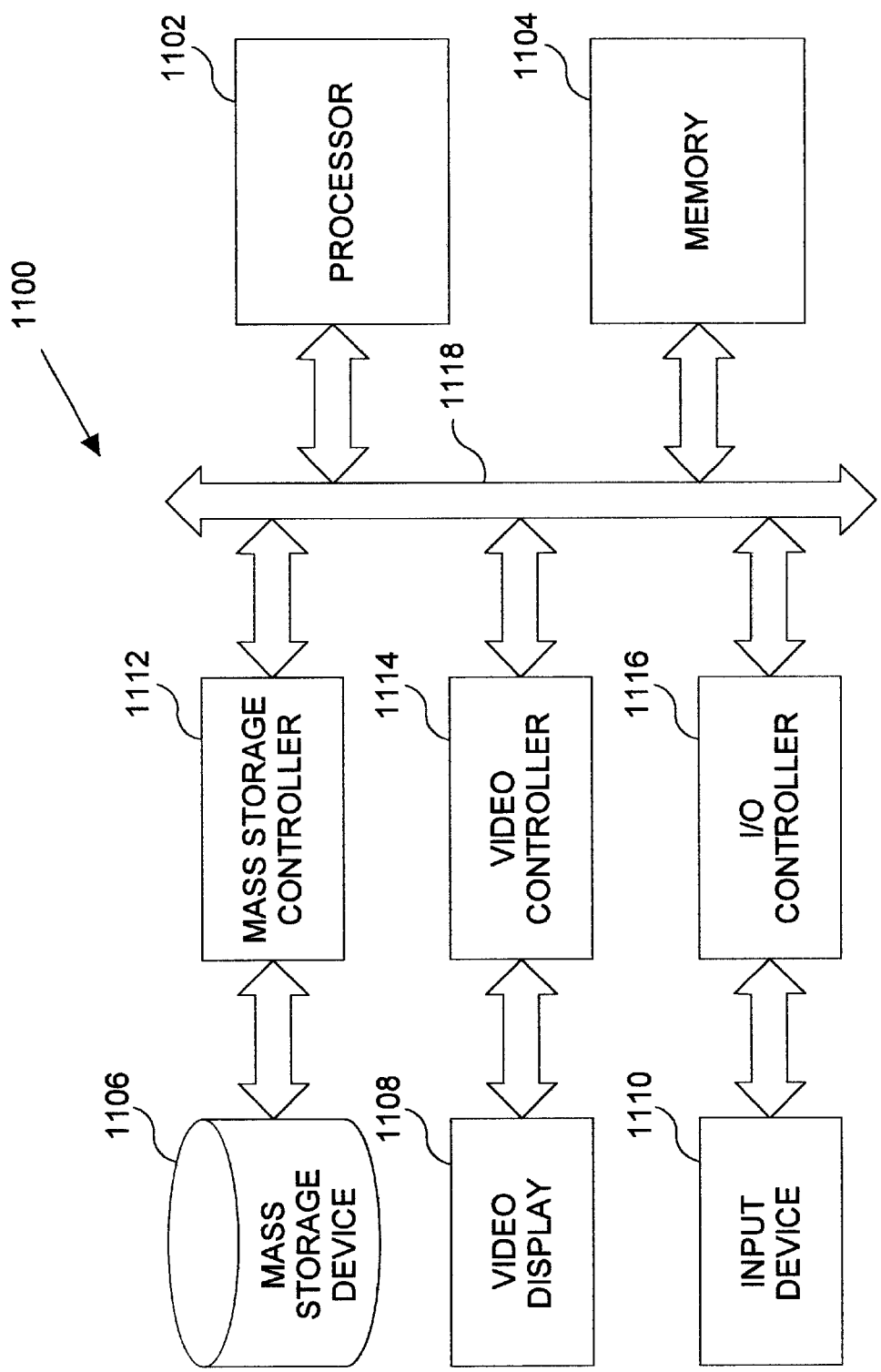
FIG. 11 shows a block diagram of a general purpose computer system which is suitable for implementing various functional blocks of the analysis system of FIG. 1.

For example, FIG. 11 illustrates a general processing system 1100 which is suitable for implementing the preprocessor 30, multiplexor 40, computational intelligence system 50, and/or the training mechanism 60 of the analysis system 10. To this end, the general processing system 1100 includes a processor 1102, memory 1104, mass storage device 1106, video display 1108, and input device 1110. Moreover, the general processing system 1100 includes a mass storage controller 1112 for controlling the mass storage device 1106, a video controller 1114 for controlling the video display 1108, an I/O controller 1116 for controlling the input device 1110, and a system bus 1118. The system bus 1118 operably couples the processor 1102 to the memory 1104, the mass storage controller 1112, the video controller 1114, and the I/O controller 1116.

The memory 1104 includes random access memory (RAM) such as SRAM (static RAM), DRAM (dynamic RAM), and SDRAM (synchronous DRAM) which store software routines obtained from computer readable media such as a floppy disk, CD-ROM disc, DVD disc, and hard disks. The memory 1104 may also include nonvolatile computer readable media such as PROM (programmable read only memory), EPROM (erasable PROM), EEPROM

TABLE 1

| Function Name | Function | Simplification |
| --- | --- | --- |
| Hyperbolic tangent | $f(x) = \tanh(\alpha x) = \dfrac{e^{\alpha x} - e^{-\alpha x}}{e^{\alpha x} + e^{-\alpha x}}$ | For small $\alpha$, $f(x) = 0$ <br> for large positive $\alpha$, $f(x) = \begin{cases} 1 & \text{if } x \geq 0 \\ -1 & \text{if } x < 0 \end{cases}$ <br> for large positive $\alpha$, $f(x) = \begin{cases} 1 & \text{if } x \geq 0 \\ -1 & \text{if } x < 0 \end{cases}$ |
| Hyperbolic secant | $f(x) = \operatorname{sech}(\alpha x) = \dfrac{2}{e^{\alpha x} + e^{-\alpha x}}$ | For small $\alpha$, $f(x) = 1$ <br> for large $\alpha$, $f(x) = 0$ |
| Gaussian Function, or Radial Basis Fuction | $f(x) = e^{\left(\frac{-x}{\alpha}\right)^2}$ | For small $\alpha$, $f(x) = 0$ <br> for large $\alpha$, $f(x) = 1$ |
| Augmented Ratio of Squares | $f(x) = \begin{cases} \dfrac{\alpha x^2}{1 + \alpha x^2} & \text{if } x > 0 \\ 0 & \text{if } x \leq 0 \end{cases}$ | For small $\alpha$, $f(x) = 0$ <br> for large $\alpha$, $f(x) = \begin{cases} 1 & \text{if } x > 0 \\ 0 & \text{if } x \leq 0 \end{cases}$ |

Exemplary Implementations of Neural Networks and Network Evolution Systems

It should be appreciated by those skilled in the art that the movement monitoring device 20, the preprocessor 30, multiplexor 40, computational intelligence system 50, and the training mechanism 60 may be implemented with various hardware components such a digital signal processors, digital logic components, and analog components. Moreover, it should be appreciated that the preprocessor 30, multiplexor 40, computational intelligence system 50, and/or the training mechanism 60 may be implemented with properly programmed general purpose computer systems, multiprocessor computer systems, and distributed clusters of computer systems.

(electrically erasable PROM), and flash memory that store firmware routines.

The processor 1102 is operable to execute the software and/or firmware routines stored in the memory 1104, and communicate with the mass storage device 1106, the video display 1108, and the input device 1110 via the mass storage controller 1112 the video controller 1114, and the I/O controller 1116 respectively. Most importantly, the processor 1102 is operable to execute software and/or firmware routines of the memory 1104 which cause the computer 1100 to implement the analysis system 10 of FIG. 1. Thus, for example, the processor 1102 may be operable to perform the functions of the preprocessor 30, the multiplexor 40, the computational intelligence system 50, the training mechanism 60 or any combination thereof.

It should be appreciated by those skilled in the art that, since the slope factors α and β may become arbitrarily large and the input signal $a_{1k}$, $a_{2k}$, and $a_{nk}$ may be arbitrarily large, precautions must be taken with a computer system implementation of the computational intelligence system 50 and the exemplary training mechanism 60 to ensure against overflow and underflow errors. For example, in an exemplary computer system embodiment of the present invention, the computer system 1100 in calculating the sigmoid activation function of equations (3) and (6) first test to see if the product of the slope factor α or β and the resulting combinatory value c is greater than a threshold number such as 90. If the product is greater than 90, then the computer system 1100 generates a value of 0 for the result of the sigmoid activation function instead of performing the rest of the sigmoid activation calculation. This threshold test insures that the computer system 1100 will not encounter an overflow or underflow error due to computational limits inherent to digital computations.

While the invention has been illustrated and described in detail in the drawings and foregoing description, such illustration and description is to be considered as exemplary and not restrictive in character, it being understood that only the exemplary embodiments have been shown and described and that all changes and modifications that come within the spirit of the invention are desired to be protected.

What is claimed is:

1. A method of diagnosing patients suspected of having a neurological disorder, comprising the steps of:
   a) monitoring movement of a patient in order to obtain movement data that is representative of said movement of said patient;
   b) processing said movement data in order to obtain an input pattern that is representative of said movement data;
   c) processing said input pattern with a computational intelligence system that has been trained to classify movement based upon a predetermined group of neurological disorder classifications; and
   d) generating with said computational intelligence system an output that is indicative of an appropriate neurological disorder classification for said patient.

2. The method of claim 1, wherein step a) comprises the steps of:
   generating an analog movement signal having an amplitude that varies with respect to time and that is representative of said movement of said patient; and
   sampling said analog movement signal at a predetermined sampling rate in order to obtain a plurality of digital samples that are representative of said movement of said patient.

3. The method of claim 1, wherein step b) comprises the steps of:
   extracting characteristics of said movement from said movement data, and
   generating said input pattern based upon said characteristics extracted from said movement data.

4. The method of claim 1, wherein step b) comprises the steps of:
   extracting first characteristics of said movement from first data of said movement data associated with a first time interval;
   extracting second characteristics of said movement from second data of said movement data associated with a second time interval; and
   generating said input pattern based upon said first characteristics and said second characteristics of said movement.

5. The method of claim 1, wherein step a) comprises the step of:
   collecting said movement data such that said movement data comprises a plurality of postural data sets that are each representative of a different postural tremor type.

6. The method of claim 5, wherein step b) comprises the steps of:
   extracting first characteristics of said movement from a first postural data set of said plurality of postural data sets;
   extracting second characteristics of said movement from a second postural data set of said plurality of postural data sets; and
   generating said input pattern based upon said first characteristics and said second characteristics.

7. The method of claim 1, wherein step b) comprises the steps of:
   extracting frequency characteristics of said movement from said movement data, and
   generating said input pattern based upon said frequency characteristics of said movement data.

8. The method of claim 1, wherein step b) comprises the steps of:
   extracting power spectral density characteristics of said movement from said movement data, and
   generating said input pattern based upon said power spectral density characteristics of said movement data.

9. The method of claim 1, wherein step b) comprises the steps of:
   extracting statistical characteristics of said movement from said movement data, and
   generating said input pattern based upon said statistical characteristics of said movement.

10. The method of claim 1, wherein step b) comprises the steps of:
    extracting first frequency characteristics of said movement from first data of said movement data associated with a first time interval,
    extracting first statistical characteristics of said movement from said first data of said movement data associated with said first time interval,
    extracting second frequency characteristics of said movement from second data of said movement data associated with a second time interval,
    extracting second statistical characteristics of said movement from said second data of said movement data associated with said second time interval, and
    generating said input pattern based upon said first frequency characteristics, said first statistical characteristics, said second frequency characteristics, and said second statistical characteristics of said movement.

11. The method of claim 1, wherein step c) comprises the step of processing said input pattern with a neural network of said computational intelligence system that is trained to classify movement.

12. The method of claim 1, wherein step c) comprises the step of:
    classifying said movement of said patient with said computational intelligence system based upon said predetermined group of neurological disorder classifications which comprises a normal tremor classification and a non-normal tremor classification.

13. The method of claim 1, wherein step c) comprises the step of:
classifying said movement of said patient with said computational intelligence system based upon said predetermined group of neurological disorder classifications which comprises a normal classification and a Parkinson's disease classification.

14. The method of claim 1, wherein step c) comprises the step of:
classifying said movement of said patient with said computational intelligence system based upon said predetermined group of neurological disorder classifications comprising a normal classification, a Parkinson's disease classification, and an essential tremor classification.

15. An analysis system for diagnosing patients suspected of having a neurological disorder, comprising:
a movement monitoring device operable to monitor movement of a patient over a collection period in order to obtain movement data that is representative of said movement of said patient over said collection period;
a preprocessor operable to generate an input pattern that is representative of said movement data collected by said movement monitoring device over said collection period; and
a computational intelligence system comprising a neural network that has been trained to classify movement based upon a predetermined group of neurological disorder classifications, said neural network operable to (i) process said input pattern generated by said preprocessor, and (ii) generate an output that is indicative of an appropriate neurological disorder classification for said patient.

16. The analysis system of claim 15, wherein said movement monitoring device comprises an actigraph operable to:
generate an analog movement signal having an amplitude with respect to time that is indicative of said movement of said patient with respect to time, and
sample said analog movement signal at a predetermined sampling rate in order to obtain a plurality of digital samples that are representative of said movement of said patient.

17. The analysis system of claim 15, wherein said preprocessor is further operable to:
extract characteristics of said movement from said movement data, and
generate said input pattern based upon said characteristics extracted from said movement data.

18. The analysis system of claim 15, wherein said preprocessor is further operable to:
extract first characteristics of said movement from first data of said movement data associated with a first time interval;
extract second characteristics of said movement from second data of said movement data associated with a second time interval;
generate said input pattern based upon said first characteristics and said second characteristics of said movement.

19. The analysis system of claim 15, wherein said movement monitoring device is further operable to collect said movement data such that said movement data comprises a plurality of postural data sets that are each representative of a different postural tremor type.

20. The analysis system of claim 19, wherein said preprocessor is further operable to:
extract first characteristics of said movement from a first postural data set of said plurality of postural data sets;
extract second characteristics of said movement from a second postural data set of said plurality of postural data sets;
generate said input pattern based upon said first characteristics and said second characteristics of said movement.

21. The analysis system of claim 15, wherein said neural network of said computational intelligence system is further operable to:
classify said movement of said patient based upon said input pattern and said predetermined group of neurological disorder classifications comprising a normal tremor classification and a non-normal tremor classification.

22. The analysis system of claim 15, wherein said neural network of said computational intelligence system is further operable to:
classify said movement of said patient based upon said input pattern and said predetermined group of neurological disorder classifications which comprises a normal classification and a Parkinson's disease classification.

23. The analysis system of claim 15, wherein said neural network of said computational intelligence system is further operable to:
classify said movement of said patient based upon said input pattern and said predetermined group of neurological disorder classifications which comprises a normal classification, a Parkinson's disease classification, and an essential tremor classification.

24. A computer readable medium that configures an analysis system for diagnosing patients suspected of having a neurological disorder, comprising a plurality of instructions which when executed by said analysis system causes said analysis system to:
generate an input pattern based upon movement data that is representative of movement of a patient over a collection period;
implement a neural network trained to classify said movement of said patient based upon a predetermined group of neurological disorder classifications;
process said input pattern with said neural network to obtain an appropriate neurological disorder classification for said patient; and
display output providing an indication of said appropriate neurological disorder classification for said patient.

25. The computer readable medium of claim 24, wherein said plurality of instructions when executed by said analysis system, further cause said analysis system to:
extract characteristics of said movement from said movement data, and
generate said input pattern based upon said characteristics extracted from said movement data.

26. The computer readable medium of claim 24, wherein said plurality of instructions when executed by said analysis system, further cause said analysis system to:
extract first characteristics of said movement from first data of said movement data associated with a first time interval;
extract second characteristics of said movement from second data of said movement data associated with a second time interval;

generate said input pattern based upon said first characteristics and said second characteristics of said movement.

27. The computer readable medium of claim 24, wherein:

said movement data comprises a first postural data set representative of a first postural tremor type, and a second postural data set representative of a second postural tremor type, and said plurality of instructions when executed by said analysis system, further cause said analysis system to:

extract first characteristics of said movement from said first postural data set;

extract second characteristics of said movement from said second postural data set;

generate said input pattern based upon said first characteristics and said second characteristics of said movement.

28. The computer readable medium of claim 24, wherein said plurality of instructions when executed by said analysis system, further cause said analysis system to:

classify said movement based upon said predetermined group of neurological disorder classifications comprising a normal tremor classification and a non-normal tremor classification.

29. The computer readable medium of claim 24, wherein said plurality of instructions when executed by said analysis system, further cause said analysis system to:

classify said movement based upon said predetermined group of neurological disorder classifications which comprises a normal classification and a Parkinson's disease classification.

30. The computer readable medium of claim 24, wherein said plurality of instructions when executed by said analysis system, further cause said analysis system to:

classify said movement based upon said predetermined group of neurological disorder classifications which comprises a normal classification, a Parkinson's disease classification, and an essential tremor classification.

* * * * *